US011513120B2

(12) United States Patent
Helman et al.

(10) Patent No.: US 11,513,120 B2
(45) Date of Patent: Nov. 29, 2022

(54) MEMBRANE BOUND REPORTER MOLECULES AND THEIR USE IN CELL SORTING

(71) Applicant: MERCK SERONO S.A., Vaud (CH)

(72) Inventors: Daniel Helman, Kiryat Ono (IL); Mira Toister-Achituv, Rehovot (IL); Meirav Bar-Shimon, Gedera (IL); Moshe Smolarsky, Rehovot (IL)

(73) Assignee: MERCK SERONO S.A, Vaud (CH)

( * ) Notice: Subject to any disclaimer, the term of this patent is extended or adjusted under 35 U.S.C. 154(b) by 1135 days.

(21) Appl. No.: 15/975,848

(22) Filed: May 10, 2018

(65) Prior Publication Data

US 2018/0328925 A1 Nov. 15, 2018

Related U.S. Application Data

(62) Division of application No. 13/995,716, filed as application No. PCT/IL2011/000956 on Dec. 19, 2011, now abandoned.

(30) Foreign Application Priority Data

Dec. 19, 2010 (IL) ........................................ 210093

(51) Int. Cl.
*C12N 15/85* (2006.01)
*G01N 33/569* (2006.01)
*C12Q 1/6897* (2018.01)
*G01N 33/58* (2006.01)
*C12N 15/79* (2006.01)

(52) U.S. Cl.
CPC ....... *G01N 33/56966* (2013.01); *C12N 15/79* (2013.01); *C12N 15/85* (2013.01); *C12Q 1/6897* (2013.01); *G01N 33/58* (2013.01); *G01N 33/582* (2013.01); *C07K 2319/035* (2013.01); *C07K 2319/20* (2013.01); *C07K 2319/70* (2013.01); *C12N 2810/40* (2013.01); *C12N 2830/20* (2013.01); *C12N 2830/40* (2013.01)

(58) Field of Classification Search
None
See application file for complete search history.

(56) References Cited

U.S. PATENT DOCUMENTS

| | | | |
|---|---|---|---|
| 5,418,147 A | 5/1995 | Huang | C07K 14/70564 435/198 |
| 5,762,905 A | 6/1998 | Burton et al. | 424/1.49 |
| 6,632,637 B1* | 10/2003 | McGrew | C07K 14/7155 435/252.3 |
| 6,919,183 B2* | 7/2005 | Fandl | C07K 14/315 435/69.3 |
| 7,132,273 B1 | 11/2006 | Choi et al. | 435/252.3 |
| 2001/0053524 A1 | 12/2001 | Ong | 435/6 |
| 2002/0019049 A1 | 2/2002 | Lok | 435/455 |
| 2002/0142355 A1 | 10/2002 | Barry et al. | |
| 2006/0057614 A1 | 3/2006 | Heintz | C07K 14/435 435/6.11 |
| 2006/0246066 A1 | 11/2006 | Morgan et al. | 424/144.1 |
| 2008/0286824 A1 | 11/2008 | Dupraz | C12N 9/1029 435/29 |
| 2009/0275110 A1* | 11/2009 | Kondo | C12N 9/93 435/252.8 |
| 2010/0209383 A1 | 8/2010 | Franz | A61K 38/193 424/85.1 |
| 2010/0292130 A1 | 11/2010 | Skerra et al. | 514/1.1 |

FOREIGN PATENT DOCUMENTS

| | | |
|---|---|---|
| JP | 2008-540569 | 11/2008 |
| WO | 2006/124668 | 11/2006 |
| WO | 2008118476 A2 | 10/2008 |
| WO | 2009/120895 | 10/2009 |

OTHER PUBLICATIONS

Parrott and Barry (Biochemical and Biophysical Research Communications, 2001, vol. 281, pp. 993-1000). (Year: 2001).*
Descamps et al (The Journal of Immunology, 2006, vol. 177, pp. 4218-4223). (Year: 2006).*
Achstetter, et al., Abstract only, A new signal peptide useful for secretion of heterologous proteins from yeast and its application for synthesis of hirudin, Gene, Jan. 1992, pp. 25-31, vol. 110(1).
Bonnycastle, et al., Assaying Phage-Borne Peptides by Phage Capture on Fibrinogen or Streptavidin, Biol. Chem., Jun. 1997, pp. 509-515, vol. 378, No. 6.
Pierleoni, et al., PredGPI: a GPI-anchor predictor, BMC Bioinformatics, Sep. 2008, pp. 1-11, vol. 9.
UniProtKB—055186 (CD59A_MOUSE), SC59A glycoprotein, accessed Mar. 1, 2017, pp. 1-8.
UniProtKB—P18181 (CD48_MOUSE), CD48 antigen, http://www.uniprot.org/uniprot/P18181, accessed Mar. 1, 2017, pp. 1-9.
Furguson, M.A.J., Cell-surface anchoring of proteins via glycosyl-phosphatidylinositol structures; Annual Reviews in Biochemistry, vol., 57, pp. 285-320, 1988.
Drisaldi et al., Mutant PrP Is Delayed in Its Exit from the Endoplasmic Reticulum, but Neither Wild-type nor Mutant PrP Undergoes Retrotranslocation Prior to Proteasomal Degradation; JBC, vol. 278, No. 24, pp. 21732-21743, 2003.
Medof et al., Cell-surface engineering with GPI-anchored proteins; FASEB Journal, vol. 10, pp. 574-586, 1996.
Abstract only, Achstetter, et al., A new signal peptide useful for secretion of heterologous proteins from yeast and its application for synthesis of hirudin, Gene, Jan. 1992, pp. 25-31, vol. 110(1).

(Continued)

*Primary Examiner* — Celine X Qian
(74) *Attorney, Agent, or Firm* — Browdy and Neimark, PLLC

(57) ABSTRACT

The present invention relates to nucleic acid molecules comprising a nucleic acid sequence encoding a membrane-bound biotin mimetic peptide (BMP) or biotin acceptor peptide (BAP). The invention also relates to a method for selection of high producer cells secreting a protein of interest.

26 Claims, 14 Drawing Sheets
Specification includes a Sequence Listing.

(56) References Cited

OTHER PUBLICATIONS

Schmidt et al., The Strep-tag system for one-step purification and high-affinity detection or capturing of proteins; Nature Protocols, vol. 2, No. 6, pp. 1528-1535, 2007.
Predonzani et al. "In vivo site-specific biotinylation of proteins within the secretory pathway using a single vector system", BMC Biotechnology Biomed Central LTD, London GB, 8(1):41 (2008).
Nesbeth et al. "Metabolic Biotinylation of lentiviral pseudotypes for scalable paramagnetic microparticle-dependent manipulation", Molecular theraphy, academic press san diego CA US, 13(4):814-822 (2006).
Tannous et al. "Metabolic biotinylation of cell surface receptors for in vivo imaging" Nature methods, 3(5) 391-396 and (2006) 3:s386.
Li Erqiu et al. "Mammalian cell expression of dimeric small immune proteins Protein engineering" oxford university press surrey GB., 10(6):731-736 (1997).
Pavlinkova et al. "Constructs of biotin mimetic peptide with CC49 single chain FV designed for tumor pretargeting" Peptides Elsevier Amsterdam, 24(3):253-362 (2003).
Luo et al. "Expression of fusion protein of scFv-biotin mimetic peptide for immunoassay" Journal of biotechnology, 65(2-3)(1998).
Puck, T.T. et al. A Rapid Method for Viable Cell Titration and Clone Production with He/a Cells in Tissue Culture: The Use of X-Irradiated Cells to Supply Conditioning Factors. Proc Natl Acad Sci USA, 41(7): p. 432-7 (1955).
Bohm, E., et al., "Screening for improved cell performance: selection of subclones with altered production kinetics or improved stability by cell sorting" Biotechnol Bioeng, 88(6): 699-706 (2004).
Jun, S.C., et al., "Selection strategies for the establishment of recombinant Chinese hamster ovary cell line with dihydrofolate reductase-mediated gene amplification." Appl Microbiol Biotechnol, 69(2):162-9 (2005).
Coller, H.A. et al. "Poisson statistical analysis of repetitive subcloning by the limiting dilution technique as a way of assessing hybridoma monoclonality" Methods Enzymol,. 121: 412-7 (1986).
Underwood, P.A. et al. "Hazards of the limiting dilution methods of cloning hybridomas" Journal of immunol. methods, 107: 119-128 (1988).
Herzenberg, L.A., et al., "The history and future of the fluorescence activated cell sorter and flow cytometry: a view from Stanford" Clin Chern, 48(10): 1819-27 (2002).
Browne, et al. "Selection methods for high-producing mammalian cell lines" Trends Biotechnol, 25(9): p. 425-32 (2007).
DeMaria, C.T., et al., "Accelerated clone selection for recombinant CHO Cells using a FACS-based high-throughput screen" Biotechnol Prog, 23(2): 465-72 (2007).
Gaines, P. et al. "p/Res-CD4t, a dicistronic expression vector for MACS- or FACS-based selection oftransfected cells" Biotechniques, 26(4): p. 683-8 (1999).
Meng, Y.G., et aL, "Green fluorescent protein as a second selectable marker for selection of high producing clones from transfected CHO cells" Gene, 242(1-2):201-7 (2000).
Yoshikawa, T., et al., "Flow cytometry: an improved method for the selection of highly productive gene-amplified CHO cells usingflow cytometry" Biotechnol Bioeng, 74(5): 435-42 (2001).
Marder, P., et al., "Selective cloning of hybridoma cells for enhanced immunoglobulin production using flow cytometric cell sorting and automated laser" nephelometry. Cytometry, 11(4): p. 498-505 (1990).
Sen, S., et al. "Flow cytometric study ofhybridoma cell culture:correlation between cell surface fluorescence and /gG production rate" Enzyme Microb Technol, 12(8): 571-6 (1990).
Brezinsky, S.C., et al., "A simple method for enriching populations of transfected CHO cells for cells of higher specific productivity", J Immunol Methods 277(1-2): p. 141-55 (2003).
Powell, K.T. et al. "Gel microdroplets and flow cytometry: rapid determination of antibody secretion by individual cells within a cell population" Biotechnology (NY), 8(4): p. 333-7 (1990).
Weaver, J.C. et al. "Gel microdrop technology for rapid isolation of rare and high producer cells" Nat Med, 3(5): p. 583-5 (1997).

Frykman; S. et al. "Quantitating secretion rates of individual cells: design of secretion assays" Biotechnol Bioeng, 59(2): 214-26 (1998).
Manz, R., et al., "Analysis and sorting of live cells according to secreted molecules, relocated to a cell-surface affinity matrix", Proc Natl Acad Sci USA, 92(6):1921-5 (1995).
Holmes, P. et al. "Improved cell line development by a high throughput affinity capture surface display technique to select for high secretors" J Immunol Methods, 230(1-2):141-7. (1999).
Koller, M.R., et al., "High-throughput laser-mediated in situ cell purification with Highpurityandyield" Cytometry A, 61(2):153-61 (2004).
Hanania, E.G., et al., "Automated in situ measurement of cell-specific antibody secretion and laser-mediated purification for rapid cloning of highly-secreting producers" Biotechnol Bioeng 91(7):872-6 (2005).
Giebel, L.B., et al., "Screening of cyclic peptide phage libraries identifies ligands that bind streptavidin with high affinities" Biochemistry, 34(47): p. 15430-5 (1995).
Katz, B.A., et al. "Binding to protein targets of peptidic leads discovered by phage display: crystal structures of streptavidin-bound linear and cyclic peptide ligands containing the HPQ sequence" Biochemistry, 34(47): p. 15421-9 (1995).
Beckett, D., et al. A minimal peptide substrate in biotin holoenzyme synthetase-catalyzed biotinylation Protein Sci, 8(4): p. 921-9 (1999).
Barker, D.F. et al. "The birA gene of *Escherichia coli* encodes a biotin holoenzymesynthetase" J Mol Biol, 146(4): p. 451-67 (1981).
Chapman-Smith, A. et al. Molecular biology of biotin attachment to proteins. J Nutr, 129(2S Suppl): 477S-484S (1999).
Mechold, U. et al. "Codon optimization of the BirA enzyme gene leads to higher expression and an improved efficiency of biotinylation of target proteins in mammalian cells" J Biotechnol, 116(3): 245-9 (2005).
Parrott, M.B. et al. "Metabolic biotinylation of secreted and cell surface proteins from mammalian cells" Biochem Biophys Res Commun, 281(4): 993-1000 (2001).
Yang, J., et al., "In vivo biotinylation of the major histocompatibility complex(MHC) class If/peptide complex by coexpression of BirA enzyme for the generation of MHC class 11/tetramers" Hum Immunol, 65(7): 692-9 (2004).
Chen, L., et al., "Site-specific labeling of cell surface proteins with biophysical probes using biotin ligase" Nat Methods, 2(2):99-104 (2005).
De Boer, E., et al., "Efficient biotinylation and single-step purification of tagged transcription factors in mammalian cells and transgenic mice" Proc Natl Acad Sci US A, 100(13): 7480-5 (2003).
Krogh, A., et al., "Predicting transmembrane protein topology with a hidden Markov model: application to complete genomes" J Mol Bioi, 305(3): p. 567-80 (2001).
Eisenhaber, B., et al. "Sequence properties of GPJ-anchored proteins near the omega-site: constraints for the polypeptide binding site of the putative transamidase" Protein Eng, 11(12): p. 1155-61 (1998).
Sunyaev, S.R., et al., "PSIC: profile extraction from sequence alignments with position-specific counts of independent observations" Protein Eng, 12(5): 387-94 (1999).
Eisenhaber, B., P. Bork, et al. "Prediction of potential GPI modification sites in proprotein sequences" J Mol Bioi, 292(3): 741-58 (1999).
Eisenhaber, B., et al., "Automated annotation of GPI anchor sites: case study C. elegans" Trends Biochem Sci, 25(7): 340-1 (2000).
Powell, M.B., et al., "Molecular cloning, chromosomal localization, expression, and functional characterization of the analogue mouse of human CD59" J Immunol, 158(4):1692-702 (1997).
Qian, Y.M., et al., "Identification and functional characterization of a new gene encoding the mouse terminal complement inhibitor CD59" J Immunol, 165(5): 2528-34 (2000).
Sugita, Y. et al. "CD59: its role in complement regulation and potential for therapeutic use" Immunotechnology, 1(3-4): 157-68 (1995).
Ikezawa, H., et al. "Glycosylphosphatidylinositol (GPI)-anchored proteins" Bioi Pharm Bull, 25(4): 409-17 (2002).

(56) References Cited

OTHER PUBLICATIONS

Nielsen, H., et al., "Identification of prokaryotic and eukaryotic signal peptides and prediction of their cleavage sites" Protein Eng, 10(1):1-6 (1997).

Bendtsen, J.D., et al., "Improved prediction of signal peptides" SignalP 3.0. J Mol Bioi, 340(4): 783-95 (2004).

Urlaub, G. et al. Isolation of Chinese hamster cell mutants deficient in dihydrofolate reductase activity Proc Natl Acad Sci US A, 77(7):4216-20. (1980).

Cockett, M.I., et al. High level expression of tissue inhibitor of metalloproteinases in Chinese hamster ovary cells using glutamine synthetase gene amplification Biotechnology (NY), 8(7): 662-7. (1990).

Page, M.J. et al. High level expression of the humanized monoclonal antibody Campath-1 H in Chinese hamster ovary cells. Biotechnology (NY), 9(1):64-8 (1991).

Barnes, L.M., et al. "Advances in animal cell recombinant protein production: GS-NSO expression system" 32(2): 109-23 (2000).

Gurtu, V. et al. "IRES bicistronic expression vectors for efficient creation of stable mammalian cell lines" Biochem Biophys Res Commun, 229(1):295-8 (1996).

Viens, A. et al., "Use of protein biotinylation in vivo for chromatin immunoprecipitation" Anal Biochem, 325(1): 68-76 (2004).

Cognet, I., et al., "Cardiotrophin-like cytokine labelling using Bir A biotin ligase: a sensitive tool to study receptor expression by immune and non-immune cells" J Immunol Methods, 301(1-2): p. 53-65 (2005).

Skerra, Use of the tetracycline promoter for the tightly regulated production of a murine antibody fragment in *Escherichia coli*; Gene, vol. 151, pp. 131-135, 1994.

Powell et al., Molecular Cloning, Chromosomal localization, Expression, and Functional Characterization of the Mouse Analogue of Human CD59; Journal of Immunology, vol. 158; pp. 1692-1702, 1997.

Katz, B.A., Streptavidin-binding and -dimerizing ligands discovered by phage display, topochemistry, and structure-based design; Biomolecular Engineering, vol. 16, pp. 57-65, 1999.

\* cited by examiner

Fig. 2A
Fig. 2B
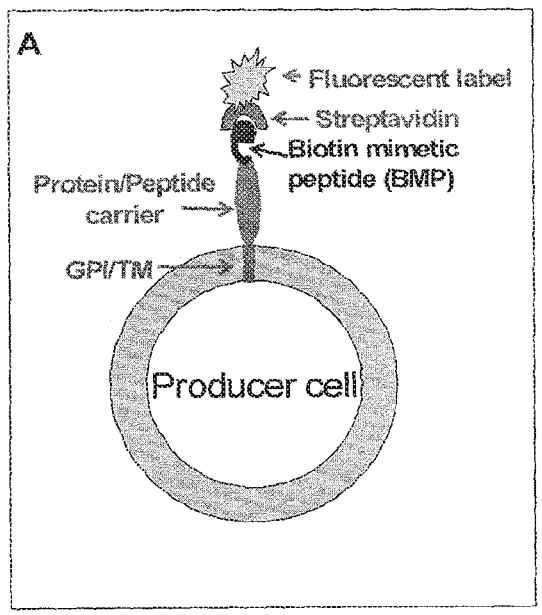
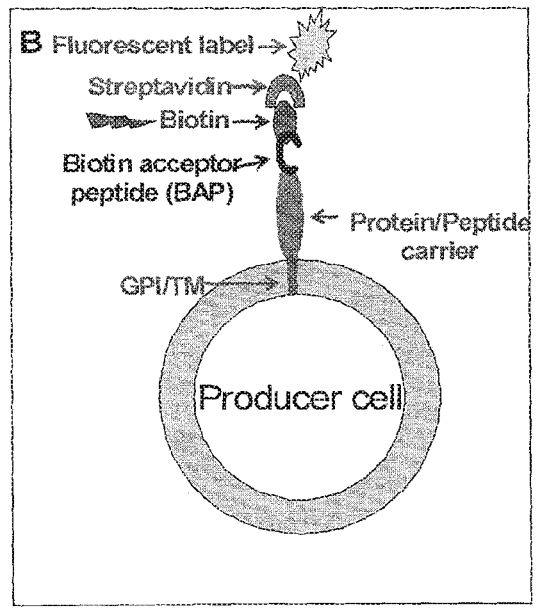
Fig. 2C
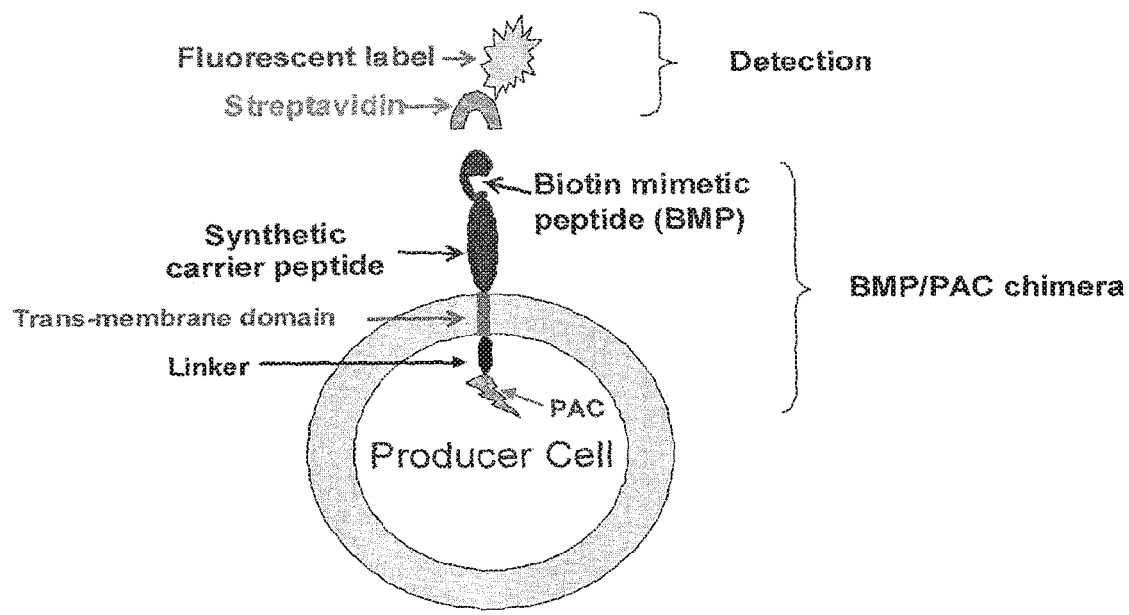

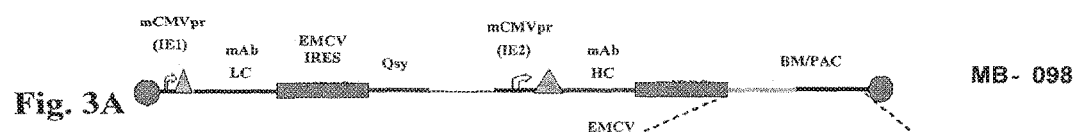
Fig. 3A
Fig. 3B
Fig. 4
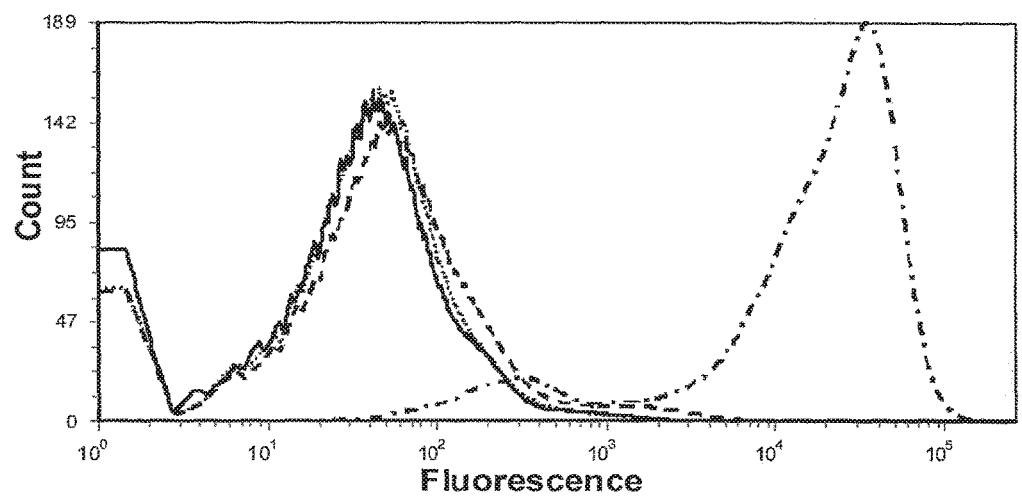

Detection: Anti-h Fc

Detection: Anti-LC (K)

MEMBRANE BOUND REPORTER MOLECULES AND THEIR USE IN CELL SORTING

TECHNICAL FIELD

The present invention relates to nucleic acid molecules comprising a nucleic acid sequence encoding a membrane-bound biotin mimetic peptide (BMP) or biotin acceptor peptide (BAP). The invention also relates to a method for selection of high producer cells secreting a protein of interest.

BACKGROUND

One of the major challenges in development of producer cells for manufacturing of recombinant proteins is the selection of high producer cells among a very large cell population, with different productivity levels, generated in the course of clone development. The selection of the high producers is usually intensive and time consuming. The number of cells that can be screened manually is limited and so is the probability to isolate the clones of the required productivity level.

Traditional methods have been employed for screening for high producer cells. One of the common manual single cell cloning techniques is the "limiting dilution" procedure. Manual picking and selection of clones by this procedure is tedious, labour intensive and a time consuming task. Even if performed by robotic systems, the number of clones that can be screened is limited [1-3]. In addition, statistical analyses indicate that repeated cloning cycles are required to ensure clonality at an acceptable level. [4, 5]. Therefore, more efficient methods of cell line selection and cloning are required.

Flow cytometry [6] has been applied for selection of cells labeled with fluorescent reporters. Some of the flow cytometry machines are able to sort thousands of cells within a few seconds and select rare cells with very low frequencies (as low as $10^{-6}$) in the entire population [7]. Another advantage of the flow cytometry is its ability, in some of the machines, to seed single cells (clone the cells) in separate wells in microtiter plates [6, 8].

However, cell sorting by flow cytometers requires a fluorescent signal. Since the protein product of interest is not fluorescent in most of the cases, a fluorogenic reporter gene product, whose expression is tightly linked to that of the gene of interest (GOI), is required.

The reporter gene product may be expressed in the cell cytoplasm or can be directed to the cell surface [8, 9].

The reporter gene can be naturally fluorescent such as GFP [10]. Alternatively, it can be specifically stained with a fluorescence marker that penetrates the cells such as fluorescent methotrexate (F-MTX) [11] or stained with a fluorescent marker that binds to it on the cell surface [8, 9].

An interesting case was reported for antibodies produced in cell culture. It has been observed that the secreted antibody itself may be used as a reporter and can be detected on the membrane of hybridoma cells [12, 13] and CHO cells [14]. Staining with fluorescently labeled anti-antibodies was used to detect the antibody on cell surface.

A further known method for isolation of specific desired cells is based on magnetic beads. Magnetic beads coated with a protein that binds specifically to a target protein on the cells' surface was previously reported [9].

Other methods based on direct detection of the secreted POI were also published. These methods include gel microdrop technology [15-17] and matrix-based secretion assays [18, 19].

In addition, automated systems for cell selection also exist and include Laser enabled analysis and processing (LEAP) which destroys undesired cells [20, 21] and automated colony pickers such as ClonePix from Genetix and CellCelector™ from Aviso which select directly the high producers according to their secretion levels.

Besides the various pros and cons of each method, their capacity for the number of cells that can be screened is limited, and significantly lower than that obtained by the e.g. Fluorescence-activated cell sorting (FACS).

SUMMARY OF INVENTION

The present invention comprises coupling protein of interest (POI) expression to that of a cell surface membrane protein/peptide marker labeled with biotin mimetic or biotin acceptor peptides. Following staining with a fluorescently labeled biotin-binding protein, the cells are sorted by an appropriate technique as discussed below.

The present invention relates, in one aspect, to a nucleic acid molecule comprising:
(a) a first nucleic acid sequence encoding a signal peptide linked at its C-terminal to
(b) a second nucleic acid sequence encoding a biotin mimetic peptide (BMP) or a biotin acceptor peptide (BAP), linked at its C-terminal to
(c) a third nucleic acid sequence encoding a polypeptide stretch that allows the anchorage of the BMP or BAP to a cell membrane.

In a related aspect, the present invention provides a vector comprising the nucleic acid molecule as defined above.

The invention also relates to a protein encoded by the above nucleic acid molecules.

In another aspect, the present invention relates to a method for the selection of eukaryotic cells secreting a protein of interest (POI), comprising identifying cells presenting BMP on their cell surface, wherein the level of BMP presentation on the cell surface is correlated with the amount of POI secreted, the method comprising the steps of:
(a) transfecting cells with a vector comprising either
  i. the nucleic acid molecule comprising the first, second and third nucleic acid sequences above and a second nucleic acid molecule comprising a POI-encoding nucleic acid sequence; or
  ii. a nucleic acid molecule comprising both nucleic acid molecules on the same vector, thereby establishing a stable pool of BMP transfected cells;
(b) labeling the BMP transfected cells with a detectable biotin-binding moiety; and
(c) identifying and isolating transfected cells labeled with the detectable biotin-binding moiety.

In another aspect, BAP is employed instead of BMP. In this case BirA and biotin need to be added prior to labeling of the cells.

Improvement of the above system is obtained by fusing a polypeptide conferring selection resistance to the polypeptide stretch that allows anchoring the BMP reporter. Applying selection pressure post transfection selects transfected cells expressing the resistance gene. Since the selection resistance gene is fused to the BMP reporter gene, such application of selection is also efficient for high BMP expressing cells at early stages before sorting is done and may be efficient for selection of the highest POI producer cells in the population as well.

Thus, in certain embodiments, the polypeptide stretch that allows the anchorage of the BMP or BAP to a cell membrane is linked at its carboxyl terminus to a polypeptide conferring selection resistance.

BRIEF DESCRIPTION OF THE DRAWINGS

FIGS. 2A-C show the structures of reporter molecules on cell surface. Illustration of biotin mimetic peptide (BMP, panel A) and biotin acceptor peptide (BAP, panel B) fused to their membrane anchored carrier on cell surface. Anchorage to the membrane is obtained via glycosyl phosphatidylinositol (GPI) or by a trans-membrane peptide (TM). BMP is stained directly with fluorescent streptavidin (F-SA). BAP is first biotinylated by biotin protein ligase (BirA), followed by staining with F-SA. FIG. 2C shows a biotin mimetic peptide (BMP) and puromycin N-acetyl transferase (PAC) fusion protein (BMP-PAC). Anchorage to the membrane obtained via a trans-membrane peptide (TM). PAC is used for puromycin selection and BMP is stained directly with fluorescent streptavidin (F-SA) for FACS selection and analysis.

FIGS. 3A-B is an illustration of a BMP-PAC expression vector (A) comprising the BMP-PAC reporter gene (B). The vector was constructed for evaluation of the BMP-PAC reporter gene by FACS technology. mCD59aSP—signal peptide from murine CD59a; BMP—Biotin mimetic peptide; Synthetic carrier—a carrier peptide of 60 amino acids; IGF1-R-TM domain—trans-membrane domain from IGF1 receptor, PAC—Puromycin N-acetyl transferase; mAb—monoclonal antibody; LC—light chain; HC—heavy chain, mCMVpr—murine immediate CMV—early-gene promoters.

FIG. 4 shows detection of BAP on cell surface with fluorescent streptavidin (F-SA) by FACS. CHO-S cells, non-transfected and not stained (—, MFI—66). CHO-S cells, non-transfected, incubated with BirA and stained with F-SA ( . . . , MFI—69). CHO-S transfected with plasmids expressing BAP-CD59a reporter gene, not incubated with BirA and stained with F-SA (- - -, MFI—139). CHO-S transfected with plasmids expressing BAP-CD59a reporter gene, incubated with BirA and stained with F-SA (- . . -, MFI—24364).

DETAILED DESCRIPTION OF THE INVENTION

Figure 1:
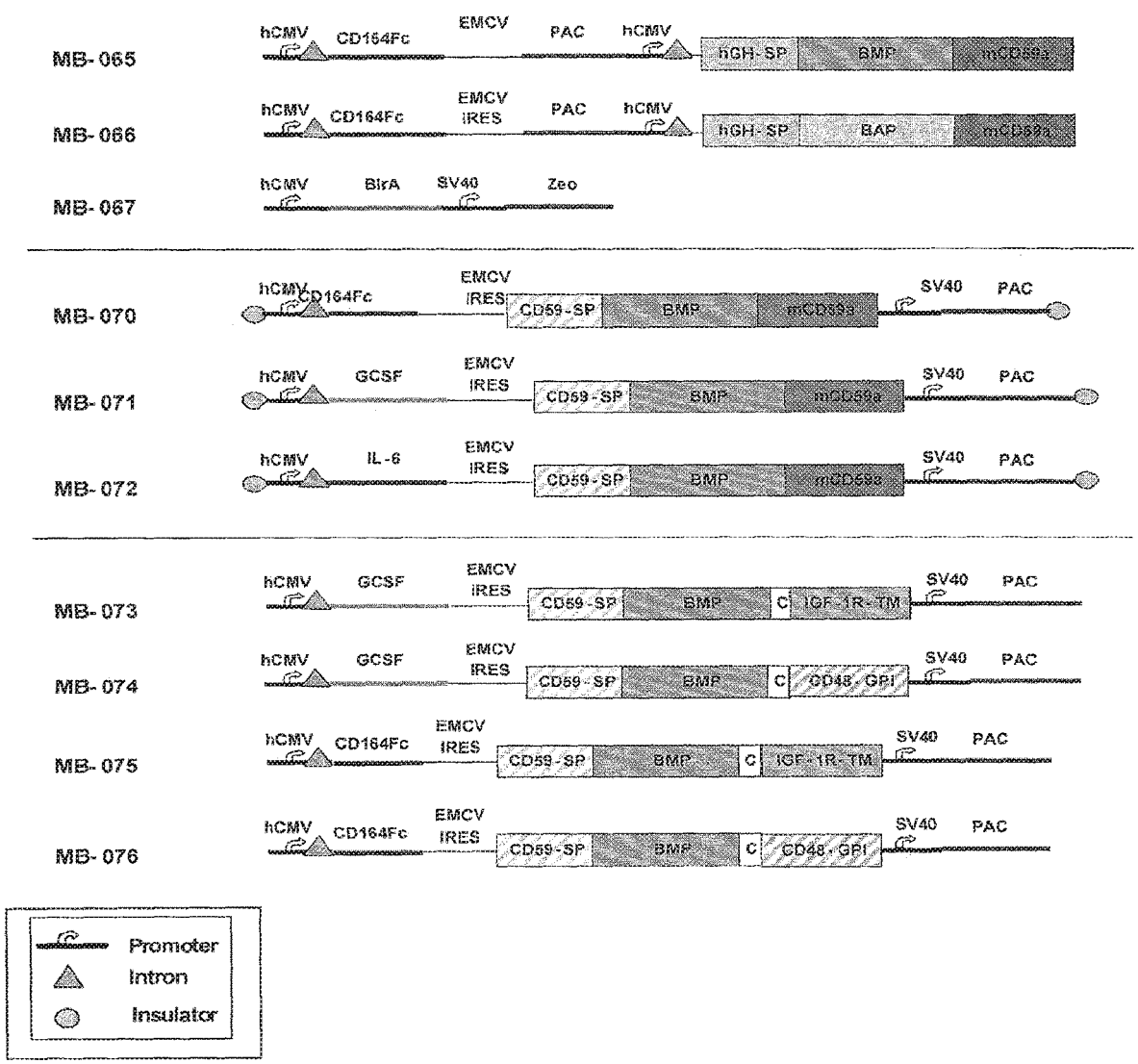
FIG. 1 shows vectors containing novel reporter genes for FACS clone development. The vectors were constructed for evaluation of novel reporter genes by FACS technology. BMP—Biotin mimetic peptide; SP—signal peptide; TM—trans-membrane domain; PAC—puromycin resistance gene; C—peptide carrier motif; CD48-glycosyl phosphatidylinositol—GPI sequence taken from CD48. hGH—human growth hormone; mCD59a—GPI sequence taken from mouse CD59a; hCMV—Human Cytomegalovirus immediate early promoter; SV 40—Simian vacuolating virus 40 promoter; IGF-1R—insulin like growth factor-1 receptor; EMCV—Encephalomyocarditis virus; IRES—Internal Ribosome Entry Site; CD164-Fc—an Fc fusion of sCD164, GCSF—Granulocyte colony-stimulating factor; IL6—interleukin 6.

Cell sorting by flow cytometry, e.g. FACS, requires a fluorsescent signal. Since a protein of interest (POI) is usually not fluorescent, a fluorogenic reporter gene product, the expression of which is linked to the expression of the gene of interest (GOI) is required.

The biotin-streptavidin system of labeling cell surface marker is advantageous for several reasons: 1) the system is applicable to many cell types with low background; 2) the affinity and specificity of biotin binding to streptavidin is very high; and 3) the system conforms with "animal component free" conditions, and does not require the use of antibodies which may require a separate file to the regulatory authorities Since biotin is not a protein or a peptide and therefore cannot be encoded by a specific DNA sequence, two strategies were taken: 1) utilization of a peptide that mimics biotin in its ability to bind streptavidin (BMP) [22, 23], and 2) employment of a synthetic biotin acceptor peptide (BAP) [24] that can be specifically biotinylated by a biotin protein ligase (BPL), such as BirA, derived from bacterial origin [25, 26] that is either transfected into the cells as an encoding DNA [27-29] or added as a protein to the enzymatic mixture [24, 30, 31]. The synthetic BAP sequence [24] is specifically biotinylated similarly to the longer natural sequence [26] by the enzyme BPL [26].

For enabling detection of the reporter with the F-SA on a cell surface, after being processed through the same secretion machinery used by the cell for processing and secretion of the POI, the reporter was designed to be bound to a cell membrane protein, processed by the secretory pathway in the ER and Golgi system. Since BMP and BAP do not have membrane attachment sequences, according to the present invention there are employed membrane bound sequences that are relatively short, can be easily expressed, are not normally expressed on CHO cells, are not known to be cytotoxic and do not have known negative biological effects on the cell.

Prediction of transmembrane domain sequences is well known in the art. It can be carried out, for example by using the TMHMM server v.2.0 [32] or for GPI anchored sequence by using the GPI modification site prediction [33-36].

For the purpose of example only, two membrane anchors were chosen. One was the murine membrane protein CD59a which includes glycosyl phosphatidylinositol (GPI), a small protein of 124 amino acids [37] that was reported to be expressed well in CHO cells and detected by FACS [38]. Additional reports in the literature on its bioactivity in protecting cells from the complement lytic effect [39] does not indicate cytotoxicity risk. It is anchored to the external side of the cell membrane by GPI [40] and it does not have an internal cytoplasmic domain that could trigger signal transduction processes.

An additional membrane anchored protein is based on a synthetic peptide sequence of 60 amino acids and two potential N-glycosylation sites close to its C-terminus, and either a GPI anchorage sequence, or a transmembrane (TM) sequence.

As mentioned above, in one aspect, the present invention provides a nucleic acid molecule comprising: (a) a first nucleic acid sequence encoding a signal peptide linked at its C-terminal to (b) a second nucleic acid sequence encoding a biotin mimetic peptide (BMP) or a biotin acceptor peptide (BAP) linked at its C-terminal to (c) a third nucleic acid sequence encoding a polypeptide stretch that allows the anchorage of the BMP or BAP to a cell membrane.

In one embodiment, the nucleic acid sequences of (a) and (b) and/or (b) and (c), respectively, are linked by a nucleic acid sequence encoding a peptide linker.

In a further embodiment, the polypeptide stretch that allows the anchorage of the BMP or BAP to a cell membrane is CD59a which includes its GPI.

In another embodiment the polypeptide stretch which allows the anchorage of the BMP or the BAP to a cell membrane is the synthetic carrier peptide of amino acid SEQ ID NO: 1 directly linked to CD48-GPI.

In yet another embodiment the polypeptide stretch which allows the anchorage of the BMP or the BAP to a cell membrane is the synthetic carrier peptide of amino acid SEQ ID NO: 1 directly linked to a transmembrane peptide.

In a preferred embodiment, the transmembrane peptide is the transmembrane peptide of IGF-1R of the amino acid sequence of SEQ ID NO: 2.

As mentioned above, the BMP or BAP is linked at its N-terminus, optionally via a peptide linker, to a signal peptide. The signal peptide may have any amino acid sequence that would direct the reporter to the cell membrane, an organelle membrane or outside of the cell. The sequence may be easily predicted, for example by using algorithms as taught in the literature [41,42].

Thus, in one embodiment, the BMP or BAP is linked at its N-terminus to the signal peptide via a linker peptide, and the signal peptide is a signal peptide of a protein selected from the group consisting of an antibody, a cytokine, a hormone, a growth factor, a neurotransmitter, an enzyme, a receptor ligand, a toxin, or a functional fraction thereof. The signal peptide may also be the native or endogenous signal peptide of the protein of interest or the one of human growth hormone or of CD59.

The ability to bio-select for transfected cells, to sort cells expressing the highest levels of the reporter gene and by that to select the cells producing the highest level of protein of interest may be improved by fusing a polypeptide conferring selection resistance to the reporter in this way, the correlation between the resistance of the cells to the selection agent of choice, the expression of the reporter and the expression of the protein of interest is increased. Moreover, bio-selection is applied a short time post transfection and before sorting, and this insures that most of the resistant population would express the selection resistance gene, the reporter gene and the GOI.

Thus, in a further embodiment, the polypeptide stretch that allows the anchorage of the BMP to a cell membrane is linked at its carboxyl terminus to a polypeptide conferring selection resistance. This polypeptide is selected from the group consisting of an antibiotic-hydrolyzing enzyme, an antibiotic-scavenging protein, e.g. the Sh ble gene product that binds to and inhibits activity of Zeocin, and an antibiotic modifying enzyme such as a kinase. Alternatively, selection can be done by introduction of metabolic enzymes that are absent in the cells or exist at very low levels and removal of these metabolites or the sources of the metabolites from the growth medium. Two known examples are the dihydrofolate reductase (DHFR) [43] and the glutamine synthetase (GS) [44] systems. Increased selection pressure and amplification that results in overproduction is obtained in the above examples by addition to the growth medium of methotrexate for the DHFR system [45] or methionine sulphoximine for the GS system [46].

In one embodiment, the polypeptide stretch that allows the anchorage of the BMP or BAP to a cell membrane is linked to the antibiotic-hydrolyzing enzyme via a linker peptide.

In another embodiment, the antibiotic-inactivating enzyme is selected from the group consisting of a puromycin-inactivating enzyme, such as puromycin N-acetyl transferase (PAC) and an aminoglycoside (e.g. Geneticin) hydrolyzing enzyme, such as aminoglycoside 3'-phosphotransferase; the antibiotic-scavenging protein is an Sh ble gene product; and the antibiotics modifying enzyme is a hygromycin kinase.

The linkage between the BMP or BAP to the polypeptide stretch that allows their anchorage to a cell membrane, the linkage between the BMP or BAP and their signal sequences and the linkage between the polypeptide stretch and the polypeptide conferring selection resistance may be direct or via a linker peptide.

In a preferred embodiment, the linker peptide consists of the amino acid sequence of isoleucine and proline or it consists of an amino acid sequence of SEQ ID NO: 4 ((G$_4$S)n(G4)m, wherein n is an integer selected from 1, 2, 3, 4, or 5, in particular it is 2 or 4; and m is an integer selected from zero or 1.

In another embodiment, the nucleic acid molecule of the present invention is operably linked to a promoter, such as hCMV, capable of driving the transcription of the nucleic acid molecule, and is optionally operably linked downstream to an EMCV IRES sequence.

As shown hereinafter in the examples, several plasmids were constructed with different genes of interest (GOIs), and either the genes for BMP or BAP reporters fused to the membrane anchored carriers. The GOIs and the reporter genes were linked by an internal ribosome entry site (IRES). In those plasmids the GOI expression is driven by the powerful human CMV (hCMV) promoter and the reporter gene is located downstream to the IRES. The GOI expression may also be driven by any strong promoter, apart from hCMV, such as, but not limited to murine CMV IE1 or murine CMV IE2, which were used herein below to drive the expression of the light and heavy chains of an IgG antibody. This bicistronic architecture dictates transcription of both genes on the same mRNA [47].

In order to biotinylate the BAP sequence the cells were either co-transfected with the bacterial BirA expression vector [27] to obtain biotinylation by the transfected cell itself [27-29, 31, 48], or the BAP was biotinylated externally by addition of biotin and BirA in a specific reaction buffer [30, 49].

Eukaryotic cells, such as CHO-S cells were transfected with the plasmids and stable pools were selected. Specific expression of BAP and BMP in transfected cells detected with fluorescent streptavidin (F-SA) was demonstrated without significant background. Furthermore, with the BMP as a reporter three consecutive sorts by FACS for high expressers were done and significant improvement in the expression level of the GOIs was obtained.

In a preferred embodiment, the plasmid, i.e. the nucleic acid molecule of the invention, comprises a nucleic acid sequence that encodes for a BMP, in particular to BMP comprising the amino acid sequence of SEQ ID NO: 5, and specifically to BMP of SEQ ID NO: 5.

In one embodiment, the nucleic acid molecule comprises further nucleic acid sequences (plasmid MB-098) encoding the synthetic carrier peptide of the amino acid sequence of SEQ ID NO: 1 directly linked to the transmembrane peptide of the amino acid sequence of SEQ ID NO: 2, the signal peptide of CD59a of the amino acid sequence of SEQ ID NO: 6, and PAC of the amino acid sequence of SEQ ID NO: 7. In particular, this nucleic acid molecule comprises the nucleic acid sequence of SEQ ID NO: 8, which encodes for the BMP linked at its carboxyl terminus directly to the synthetic carrier peptide that is directly linked at its carboxyl terminus to the transmembrane peptide that is linked at its carboxyl terminus via a $(G_4S)_4$ sequence to PAC, and said BMP is linked at its amino terminus via an isoleucine-proline linker peptide to mouse CD59a signal peptide.

In another embodiment, the nucleic acid molecule comprises further nucleic acid sequences (plasmids MB-070-MB-072) encoding (in addition to BMP of the amino acid sequence of SEQ ID NO: 5) for mouse CD59a of the amino acid sequence of SEQ ID NO: 9, and the signal peptide of CD59a of the amino acid sequence of SEQ ID NO: 6. In particular, this nucleic acid molecule comprises the nucleic acid sequence of SEQ ID NO: 10, which encodes for the BMP linked at its carboxyl terminus via a $(G_4S)_2G_4$ sequence (SEQ ID NO: 4) to mouse CD59a and at its amino terminus via an isoleucine-proline linker peptide to the cognate CD59a signal peptide.

In still another embodiment, the nucleic acid molecule comprises further nucleic acid sequences (plasmids MB-073 and MB-075) encoding (in addition to BMP of the amino acid sequence of SEQ ID NO: 5) for the synthetic carrier peptide of the amino acid sequence of SEQ ID NO: 1 directly linked to the transmembrane peptide of the amino acid sequence of SEQ ID NO: 2, and the signal peptide of CD59a of the amino acid sequence of SEQ ID NO: 6. In particular, this nucleic acid molecule comprises the nucleic acid sequence of SEQ ID NO: 11, which encodes for the BMP linked at its carboxyl terminus directly to the synthetic carrier peptide that is directly linked at its carboxyl terminus to the transmembrane peptide and said BMP is linked at its amino terminus via an isoleucine-proline linker peptide to the mouse CD59a signal peptide.

In yet another embodiment, the nucleic acid molecule comprises further nucleic acid sequences (plasmids MB-074 and 076) encoding (in addition to BMP of the amino acid sequence of SEQ ID NO: 5) for the synthetic carrier peptide of the amino acid sequence of SEQ ID NO: 1 directly linked to the CD48-GPI anchor peptide of the amino acid sequence of SEQ ID NO: 3, and the signal peptide of CD59a of the amino acid sequence of SEQ ID NO: 6. In particular, this nucleic acid molecule comprises the nucleic acid sequence is of SEQ ID NO: 12, which encodes for a BMP directly linked at its carboxyl terminus to a synthetic carrier peptide that is directly linked at its carboxyl terminus to CD48-GPI anchor peptide and said BMP is linked at its amino terminus via an isoleucine-proline linker peptide to mouse CD59a signal peptide.

According to the present invention the reporter gene product and the protein of interest may be encoded by nucleic acids on separate plasmids, or they may be encoded by nucleic acids on the same plasmid.

When the reporter gene product and the POI are encoded by nucleic acids on separate plasmids, the cells are cotransformed with both, the plasmid containing the reporter gene and the a second plasmid including the gene coding for the POI.

When one plasmid is employed, the present invention provides a nucleic acid molecule comprising (a) a first nucleic acid sequence encoding a signal peptide; (b) a second nucleic acid encoding a biotin mimetic peptide (BMP) or a biotin acceptor peptide (BAP); (c) a third nucleic acid encoding a polypeptide stretch that allows the anchorage of the BMP or BAP to a cell membrane; and (d) a POI-encoding nucleic acid sequence.

In one embodiment, the POI-encoding nucleic acid sequence is operably linked upstream to an EMCV IRES sequence or downstream to a promoter capable of driving the transcription of the nucleic acid molecule, or both.

According to another embodiment several POI-encoding nucleic acid sequences may be present coding for several different subunits of a multi-subunit protein. Thus, for example, a cytokine of interest would be encoded by a single POI-encoding nucleic acid sequence while an IgG or IgM would be encoded by two or three POI-encoding nucleic acid sequences, respectively.

In one embodiment, the POI-encoding nucleic acid sequence is one POI-encoding nucleic acid sequence coding for a single polypeptide, while in another embodiment the at POI-encoding nucleic acid sequence comprises two nucleic acid sequences coding for different subunits of an antibody. In many cases the protein of interest should be secreted to the medium, and therefore in those cases it may be linked at its amino terminus, optionally via a linker peptide, to a signal peptide.

The protein of interest may be any protein that can be expressed in a eukaryotic cell. As non-limiting examples, and just to illuminate which proteins may be considered as protein of interest, the protein of interest is selected from the group consisting of an Fc-fusion product, an antibody, a cytokine, a hormone, a growth factor, a neurotransmitter, an enzyme, a receptor ligand, a sialomucin, a nuclear protein, a regulatory protein and a toxin, or a functional fraction thereof, i.e. a fraction of the protein which itself is an antibody (for example an Fab), a cytokine, a hormone, a neurotransmitter, an enzyme, a receptor ligand, a sialomucin or a toxin. An Fc-fusion product is a protein expressed as a fusion to a signal peptide and the Fc fragment of immunoglobulin as the N-terminal or C terminal fusion partner, which facilitates expressing and secreting high levels of many different types of POIs, as described above. The Fc domain helps to improve solubility of hydrophobic proteins and provides a handle for easy detection and purification of the fusion proteins; and it can be cleaved off by treatment with protease, if desired.

It has been found in accordance with the present invention that high producer cells that express various proteins of interest, such as a Fc-fusion product (sCD164-Fc), an antibody (anti-IL22RA mAb), a growth hormone (granulocyte colony-stimulating factor (GCSF)) or a cytokine (IL6) and express high levels of these proteins can be efficiently isolated by selecting for cells that express high levels of BMP on their surface. In still another aspect, the present invention provides a method for the selection of eukaryotic cells secreting a protein of interest (POI), comprising identifying cells presenting BMP on their cell surface, wherein the level of BMP presentation on the cell surface is correlated with the amount of POI secreted, the method comprising the steps of:

(a) transfecting cells either with a vector comprising
   (i) a nucleic acid molecule comprising the first, second and third nucleic acid sequences above and a second nucleic acid molecule comprising a POI-encoding nucleic acid sequence; or (ii) a nucleic acid molecule comprising both nucleic acid molecules under (i) above, thereby establishing a stable pool of BMP transfected cells;

(b) labeling the BMP transfected cells with a detectable biotin-binding moiety; and (c) identifying and isolating transfected cells labeled with the detectable biotin-binding moiety.

In certain embodiments, each one of said at least one POI-encoding nucleic acid sequence is operably linked upstream to an EMCV IRES sequence and downstream to a promoter capable of driving the transcription of the nucleic acid molecule, or both.

The cells used for the production of the protein of interest may be any eukaryotic cell amenable to genetic manipulations, such as mammalian, plant, insect or yeast cells. Mammalian cells may be Chinese Hamster Ovary (CHO) cells, baby mouse myeloma NS0 cells, hamster kidney (BHK) cells, human embryo kidney (HEK) cells, human retinal cells, COS cells, SP2/0 cells, WI38 cells, MRC5 cells, Per.C6 cells. Plant cells can be tobacco, carrot and rice cells. In one embodiment, the cells are CHO cells.

In certain embodiments, the cells are labeled by contacting them with a detectable biotin-binding protein or moiety selected from the group consisting of fluorescent avidin and fluorescent streptavidin and the labeled cells are then identified and isolated by the means of a FACS. However, any method could be used to identify and isolate the labeled cells, for example, but not limited to, a method using beads coated with a biotin-binding moiety.

The method of the present invention provides for a high correlation between the amount of reporter gene product expressed on the surface of the cells and the amount of protein of interest expressed and secreted, and thus enables the selection of high producer cells by isolating cells that display high levels of reporter gene product. In particular, the selected eukaryotic cells are presenting higher amounts of BMP on their surface and are secreting larger amounts of protein of interest than the transfected cells of the stable pool. In certain embodiments, the amounts of BMP on the surface of the selected eukaryotic cells and the amounts of protein of interest secreted by the selected eukaryotic cells are larger by a factor ranging between 2 and 30-fold, i.e. at least by a factor selected from the group consisting of 2, 3, 4, 5, 6, 7, 8, 9, 10, 11, 12, 13, 14, 15, and up to 30-fold-fold higher than the transfected cells of the stable pool.

The membrane-bound reporter molecules of the present invention have been found, as shown hereinafter, to be efficient for sorting high producer cells by FACS. Several important conclusions are derived from the results: the BMP and BAP reporter proteins could be specifically detected in the transfected cells; the background staining of labeled non-transfected cells was found to be negligible and therefore these reporters are suitable for selection of the required cells (Example 3); The invention provides the ability to sort cells expressing the highest levels of the reporter gene and by that to select the cells producing the highest level of POI. The method was demonstrated with several membrane anchored scaffolds and several GOIs. Productivity was increased from the pool stage to pool after three rounds of sorting cycles 1.7-13.5 fold (see table1) with different proteins and different reporter structures. Additional sorting cycle along with cloning step done by the FACS according the same reporters expression levels may even further increase the POI productivity levels in selected clones. These results strengthen the validity of the system. The reporter structure facilitates convenient staining with fluorescent-streptavidin. The fluorescent-streptavidin used in these experiments was confirmed to be of non-animal derived origin which facilitates to use this reagent in a clone development process. An important development of the basic platform was the fusion of the membrane-bound reporter molecule to the PAC selection gene; this construct was found to be very efficient for bioselection and sorting of high producer cells by FACS. It is important to point out the following: the PAC selection resistance gene was found to be active as a membrane bound protein even though naturally the enzyme is located in the cytoplasm; productivity increased during sorting cycles up to ~3 fold in pools (~11 PCD) as compared with at the start of the sorting cycles. Further increase was obtained in clones with values up to 6 fold in ProCHO5 medium (26 PCD). These results indicate that the expression of the reporter is tightly linked to that of the POI.

The invention will now be illustrated by the following non-limiting examples:

EXAMPLES

Materials and Methods.

Cells.

CHO-S(GibcoBRL, Cat. #11619) cells adapted to CHO DHFR⁻ Medium powder, SAFC (Biosciences Cat. #C6614).

Reagents

AccuPrime Pfx Invitrogen DNA Polymerase Cat No. 12344-024

Acetic Acid (glacial) Merck Cat. #K28351556 (Germany).

Acrylamide gels—NuPAGE; 10% Tris gel, Cat. #NP0301BOX, Invitrogen, (USA).

Agarose IBI Cat. #IB70042

Ampicillin—Sigma Cat. #A9518

Antibodies for ELISA:

Capture: Goat anti-human IgG (H+L), Cat. #109-005-088 Jackson Immuno Research (USA). Detection: Goat anti-human IgG Fab HRP, Cat. #109-036-098 Jackson Immuno Research (USA).

Antibody for Western Blot:

Staining: A) Goat anti-Human IgG Fc HRP, Jackson Cat. #109-036-098; B) Goat anti-Human kappa light chain, SouthernBiotech Cat. #2060-01 followed by Donkey anti-goat HRP, Jackson Cat. #705-015-147.

Blotting paper GB002 Cat. #426677 Schleicher and Schuell (USA).

Bovine serum albumin (BSA), Bovostar. Bovogen Cat. #BSAS.01

Bovine serum albumin (BSA), Sigma Cat. #A-4503

Bromophenol blue, Merck, Cat. #2126169.

Dextrane sulfate (Sigma, Cat. #D4911),

DH5α competent bacteria, Life-Technologies Cat. #18263-012

DMSO, Merck, Cat. #K31630931

DNA ladder: 1 kb ladder for DNA, Biolabs Cat No. #3232L

DNA ladder: 100 bp ladder for DNA, Biolabs Cat No. #323 L

Electrophoresis sample buffer LDS, Invitrogen, Cat. #NP0007, (USA).

Ethanol, Merck Cat. 00983.1000.

FACS Accudrop Beads, BD, Cat. #MAB345249

Glucose, Sigma, cat. #G7021

Glutamine, Sigma, cat. #05972

Hispeed plasmid Maxi Kit, Qiagen GmbH, Germany, Cat. #12663

HT Biological Industries Cat. #03-085-1C

Hydrochloric acid 37%, Merck, Cat. #1.00314.

Hydrochloric acid, Merck, cat. #UN-1789 1.00314.2500

LB+Ampicillin plates—Hy-Labs Cat. #PD178

LB medium for bacterial growth—Hy-Labs Cat. #BP302/400S.

LipofectAmine reagent, Gibco BRL Cat. #18324-020.

L-Methionine sulfoximine (MSX), Sigma Cat. #M5379

Luminogenic substrate: ECL Amersham kit, Cat. #RPN2109.

Methanol Merck Cat. #1.06009.2500

Mgcl2—1M, SIGMA, Cat #M1028

NuPAGE MOPS running buffer, X20, InvitrogenCat. #NP0001

NuPage transfer buffer, Invitrogen Cat. #NP0006-1

NuPAGE Tris Glycin running buffer, X10, InvitrogenCat. #LC2675

Phenol red, Sigma, Cat. #P0290

Pluronic F-68, Sigma Cat. #P5556

Polyoxyethylenesorbitan Monolaurate (Tween 20), Sigma Cat #P-1379

Pre-Stained marker protein standard Cat. #LC5925, Invitrogen.

Protease inhibitor cocktail, Sigma Cat. #P8340

Pure cellulose nitrate membrane BA-85, Schleicher & Schuell, 78×90 mm, Cat. #401184.

Puromycin, InvivoGen Cat. #ant-pr-1

Reference samples Anti-IL22RA (MSB0010074/C12) was obtained from EMD (GVA) 5.9 mg/ml in PBS, pH 6.0.

Restriction enzymes were purchased from New England Biolabs.

R-Phycoerythrin-conjugated Streptavidin (SA-PE), 0.2 mg/ml, BioLegend, Cat. #405203 (see CoO in 9.3 and CoA in 9.4).

Skim Milk powder, Fluka Cat. #70166

Sodium bicarbonate, Merck Cat. #6329

Sodium carbonate, Merck Cat. #6392

Sodium phosphate, Sigma, Cat. #S-3264

SYBR Safe DNA gel stain Invitrogen, Cat #S33102, 3□l/Gel

TMB Savion diagnostics, Cat. #1928

Tween20 (Polyoxyethylene-Sorbitan Monolaurate)—Sigma Cat. #P-1379

Water R.O. (ITL)

Whatman 3 mm, Whatman Cat. #3030917

Solutions

Bleach 1% —FACSClean, Becton Dickinson cat. #340345.

PBS (ITL preparation, BR R0450V01).

PBS with 0.1% Pluronic acid.

Culture Media

CHO DllFR—cloning Medium, SAFC Bioscinces Cat. #C6366, supplemented with 4 mM L-Glutamine and 15 mg/L Phenol red, Sigma, Cat. #P0290.

ProCHO5 medium, Lonza Cat. #BE12-766Q, supplemented with 4 mM L-Glutamine and 15 mg/L Phenol red, Sigma, Cat. #P0290.

Minimum Essential Medium Eagle, Sigma, cat. #M2279.

Methods

Construction of DNA Expression Vectors.

All vectors were constructed utilizing standard molecular biology techniques as taught for example in F. M. Ausubel et al. [F. M. Ausbel, 2009 #132].

Preparation of Plasmid DNA.

Plasmid DNA was isolated using QIAGEN Hispeed plasmid Maxi Kit according to the procedure described by the manufacturer.

DNA Sequencing.

The DNA fragments prepared by a contract firm (GeneArt, Germany) and cloned into the vector by standard procedures were sequenced at Hy-Labs, Israel. DNA sequencing was performed by the fully automated 16 Capillary ABI Prism 3100 Genetic Analyzer. The sequence was analyzed in-house utilizing the Sci-Ed General software (Clone manager software, version 7.01 and Align plus 5, version 5.01).

Transfection of CHO-S Cells.

CHO-S cells in were thawed and cultured in ProCHO5 serum free medium (Lonza, Cat. #BE12-766Q) supplemented with Hypoxanthine 13.61 mg/L and Thymidine 3.88 mg/L (HTx1, Biological Industries Cat. #03-085-1B). Cells were grown in suspension in filter tubes 50 ml Bioreactor (TPP, Cat #87050), 37° C., humidified and shaken at 320 RPM. Two days prior transfection, the cells were seeded at a concentration of $0.2 \times 10^6$ cells/ml in Erlenmeyer, 500 ml, with cap (Corning, Cat. #431145). The cells were transfected by LipofectAmine (GibcoBRL Cat. #18324-020). On the day of transfection, the cells were washed; resuspended and $10 \times 10^6$ cells were seeded in 4 ml MEM (Sigma, Cat. #M2279) in Erlenmeyer 125 ml with filter cap (Corning, Cat. #431143). For each transfection with single plasmid, 20 μg linearized vector (MB-098) were used. The final DNA volume was adjusted to 100 μl in MEM. Subsequently, 100 μl LipofectAmine were added and incubated for 45 minutes at room temperature. The DNA-LipofectAmine mix was then added to the cells and incubated for 4 hours at 37° C., 5% $CO_2$ in a shaking incubator at 45 RPM. At the end of this incubation period the cells were spun down and medium was replaced with 20 ml fresh ProCHO5 (Lonza, Cat #BE 2-766Q) supplemented with Hypoxanthine 27.22 mg/L and Thymidine 7.76 mg/L (HTx2, Biological Industries Cat. #03-085-1B) in Erlenmeyer 125 ml with filter cap (Corning, Cat. #431143). The flask was incubated at 37° C. in a shaking incubator at 125 RPM for 72 hours.

Seventy two hours post transfection, the cells were collected, centrifuged and resuspended in 20 ml ProCHO5 medium supplemented with 20 μg/ml Puromycin (Invivogen, Cat. #ant-pr-1), 25 μM MSX (Sigma, Cat. #M5379) and 100 μg/ml dextrane sulfate (Sigma, Cat. #D4911) Under these selective conditions, only cells expressing the PAC gene could survive.

In Vitro Biotinylation.

Cells cultured in animal component free medium (ACFM) were washed in PBS (phosphate buffer saline) with 0.1% Pluronic acid F-68 (Sigma Cat. #P5556) and 5 mM MgCl2 (Sigma, Cat. #M1028,) and then $2 \times 10^6$ cells were incubated in PBS with 0.1% Pluronic acid F-68 (Sigma, Cat. #P5556,), 5 mM MgCl2 (Sigma, Cat. #M1028), 0.06 mM BirA (Avidity, Cat. #BirA500) 1 mM ATP (Sigma, Cat. #A6419,) and 10 mM biotin (Sigma, Cat. #B4639,) for one hour in room temperature. After incubation the cells were washed with PBS with 0.1% Pluronic acid F-68 (Sigma, Cat. #P5556,) and 5 mM MgCl2 (Sigma, Cat. #M1028).

Labeling with Fluorescent Streptavidin (F-SA).

Cells ($2 \times 10^6$) expressing BAP that were either biotinylated in vivo or in vitro or cells expressing BMP, were washed with PBS with 0.1% Pluronic acid F-68 (Sigma, Cat. P5556) and then incubated in PBS+0.1% pluronic acid F-68+R-Phycoerythrin-conjugated Streptavidin (SA-PE) (Jackson, Cat. 016-110-084) (F-SA) diluted 1:100 and incubated for 30 minutes at 37° C. with shaking at 80 RPM. Cells were then washed in PBS with 0.1% Pluronic acid F-68 and loaded on the FACSAria for analysis.

Analysis by FACS.

Cells ($2\times10^6$) expressing BMP were washed with PBS containing 0.1% Pluronic acid F-68 (Sigma, Cat. P5556) and then incubated in PBS+0.1% pluronic acid F-68+R-Phycoerythrin-conjugated Streptavidin (BioLegend, Cat. #405203) (F-SA) diluted 1:100 and incubated for 30 minutes at 37° C. with shaking at 80 RPM. Cells were then washed in PBS with 0.1% Pluronic acid F-68 and loaded on the FACSAria for analysis.

Cell Propagation.

Cell cultures were maintained in ACFM as follows: Cells were seeded into 50 ml tubes at a concentration of $0.2\times10^6$ cell/ml in 25 ml volume and incubated at 37 C on an orbital shaker ϕ25 mm at 320 rpm. Twice a week, cell number and viability were measured. The culture was passaged by centrifugation at 100 g for 5 minutes at 4° C. and cell pellet was then re-suspended in fresh pre-warmed ACFM.

Cell Propagation and Productivity in ACFM Cell culture maintenance.

Cell cultures were maintained in ACFM as follows: Cells were seeded into T-80 flasks at a concentration of $0.2\times10^6$ cell/ml and incubated at 37° C. on an orbital shaker at 45 rpm. Twice a week, cell number and viability were measured. The culture was passaged by centrifugation at 100 g for 5 minutes at 4° C. and cell pellet was then re-suspended in fresh pre-warmed ACFM.

Tissue culture flasks 25 cm2 were seeded with 8-10 ml medium and incubated on an orbital shaker f25 mm at 55 rpm. Tissue culture flasks 80 cm2 were seeded with 20-30 ml medium and incubated on an orbital shaker f25 mm at 45 rpm.

Cell Productivity in ACFM.

For specific productivity (PCD) in ACFM, cells were seeded in the specified ACFM at a concentration of $0.5\times10^6$ cells/ml, in a 50 ml tube and incubated at 37° C. on an orbital shaker (320 rpm) for 24 hours. Medium was then sampled and product concentration was determined by ELISA. The calculation was done by dividing the 24 hours titters by the average concentration of cells at seeding and after 24 hours of the experiment.

$$PCD = \frac{T}{\frac{Ci+Ce}{2}}$$

PCD—pg/cell/day
T—titer (pg/ml)
Ci—cell concentration at seeding (cells/ml)
Ce—cell concentration after 24 hrs (cells/ml)

Cell Sorting.

For FACS sorting transfected cells from united pools in ProCHO5 medium supplemented with 20 μg/ml puromycin and 25 μM MSX were used. For each sort, approximately $60\times10^6$ cells were cultured and labeled with F-SA. Cells to be sorted were labeled in PBS containing 0.1% pluronic acid F-68 and F-SA diluted 1:100 at a concentration of $4\times10^6$ cells/ml in T80 flasks and incubated, 1 hour, at 37° C. in shaking incubator at 80 rpm. After labeling, cells were collected, washed twice in PBS+0.1% Pluronic acid F-68, and re-suspended at a final concentration of $10\times10^6$ cells/ml in PBS+0.1% Pluronic acid F-68 for bulk sorting. The top 4% fluorescent cells were gated on an FSC/PE dot plot for sorting with the FACSAria flow cytometer in the 'Single cell' precision mode. The sorted cells were seeded in ProCHO5 medium supplemented with 20 μg/ml puromycin and 25 μM MSX and allowed to grow until cell viability was >=90% and viable cell number was $>70\times10^6$. At this stage analysis of fluorescence and the next sorting cycle were done. Overall, three successive sorts were done.

Cloning by FACS ACDU.

Cloning was done by the Automated Cell Deposition Unit (ACDU) device of the FACSAria cell sorter, of cells growing in ProCHO5 containing g/ml puromycin and 25 μM MSX. $2\times10^6$ cells were collected, washed twice in PBS+ 0.1% pluronic acid and labeled in 0.5 ml of SA-PE (BioLegend) at a concentration of 2 μg/ml (dilution 1:100). The cells were incubated in 24 wells plate for 30 minutes at 80 rpm in a 37° C. Following labeling, cells were collected, washed twice in PBS+0.1% Pluronic, and re-suspended in 4 ml of PBS+0.1% pluronic acid (cell concentration of ~0.1-0.2 cell/ml). The top 2.5% fluorescent cells were cloned by the ACDU, in the "Single Cell" precision mode, into 96 well plates containing 180 l/well of 80% Sigma C6366 and 20% ProCHO5 ACFM mixture for cells that were cultured in ProCHO5. The plates were analyzed by Cellavista at day 0 and then every 2-3 days for detection of wells with single colony. Two weeks after cloning, supernatants from wells in which colony growth was detected, were sampled and assayed by ELISA. Wells containing >1 colony per well were omitted. Cells were picked from the wells with the highest titers and transferred first to T25 flasks containing 4 ml of 50% Sigma C6366 and 50% ProCHo5 medium mixture without shaking. Three to five days later 2-4 ml of the 100% ProCHO5 medium was added to the T25 flasks and the cells were incubated with shaking. One to three days later 8 ml of ProCHO5 were added and the suspension was transferred to T80 flasks (total of 87.5% ProCHO5 and 12.5% C6366). One to two days later 10 ml of fresh medium were added to cells. Then cells were seeded in 25 ml fresh medium at $0.2\times10^6$ cells/ml for another growth cycle. For determining specific productivity the cells were seeded at concentration of $0.5\times10^6$ cells/ml for 24 hours at 37° C. in 50 filter tubes at 320 rpm.

ELISA for sCD164-Fc.

The following procedure was employed:

1. Microtiter plates were coated with 0.5 mg/ml with monoclonal antibody to CD164 in PBS and incubated overnight at ~4° C.

2. The plates were washed three times with washing buffer (PBS containing 0.05% of Tween 20).

3. The plates were blocked with blocking buffer (PBS containing 0.5% I-Block), 200 μl/well, for 1 hour at 37° C. with shaking.

4. After blocking, the plates were washed three times with washing buffer and 100 ml aliquots of tested samples, standard curve (0.78-50 ng/ml) and check samples in assay buffer (PBS containing 0.25% I-Block and 0.05% of Tween 20), were added to the plates and incubated for 60 min at 37° C. with shaking.

5. Plates were washed again three times with washing buffer, and 100 ml of the second antibody to the Fc portion (HRP conjugate F(ab')2 fragment goat anti human diluted 1:40,000 in assay buffer) were added to each well.

6. The plates were incubated for 60 min at 37° C. with shaking.

7. Plates were washed three times with washing buffer and 100 ml of substrate solution (TMB) were added to each well and the plates were incubated 20 min at room temperature (without shaking).

8. The reaction was stopped by adding 50 μl/well of stop solution (4N HCl).

9. The absorbance was measured at A492 nm in an ELISA reader.

10. Standard solutions were prepared by serial dilutions of the Std. SCD164-Fc from 293 HEK cells to give a standard curve range from 0.78 to 50 ng/ml (linear range was between 0.78-12.5 ng/ml) in assay buffer. A sample of crude harvest from the SCD164-Fe pool was diluted with assay buffer to obtain ~10 ng/ml and used as a check sample.

11. The optical density data results were processed and results calculated by the Magelan software.

12. The dilution of samples, preparation of standard curve dilution series, and distribution of samples on the plate was performed by a robotic sample processor.

ELISA for GCSF.

The following procedure was employed:

1. Microtiter plates were coated with 1 µg/ml with monoclonal antibody to GCSF in PBS and incubated overnight at ~4° C.
2. The plates were washed three times with washing buffer (PBS containing 0.05% of Tween 20).
3. The plates were blocked with blocking buffer (PBS containing 1% BSA), 200 µl/well, for 1 hour at 37° C. with shaking.
4. After blocking, the plates were washed three times with washing buffer and 100 ml aliquots of tested samples, standard curve samples and check samples were added to the plates and incubated for 60 min at 37° C. with shaking.
5. Plates were washed again three times with washing buffer, and 100 ml of the detection biontinylated antibody anti-human GCSF solution, were added to each well.
6. The plates were incubated for 60 min at 37° C. with shaking.
7. The plates were incubated with a second antibody, Streptavidin HRP, following the same procedure described in steps 5-6 above.
8. Plates were washed three times with washing buffer.
9. 100 ml of substrate solution (TMB) were added to each well and the plates were incubated 20 minutes at room temperature (without shaking).
10. The reaction was stopped by adding 50 µl/well of stop solution (3N HCl).
11. The absorbance was measured at 492 nm in an ELISA reader.
12. Standard solutions were prepared by serial dilutions of the Standard recombinant human GCSF to give a standard curve of 1.56-100 ng/ml (linear range was between 3-50 ng/ml).
13. The optical density data results were processed and results calculated by the Magelan software.
14. A robotic sample processor performed the dilution of samples, preparation of standard curve dilution series, and distribution of samples on the plate.

ELISA for IL-6 The following procedure was employed:

1. Microtiter plates were coated with 1 mg/ml with monoclonal antibody to IL6 in PBS and incubated overnight at ~4° C.
2. The plates were washed three times with washing buffer (PBS containing 0.05% of Tween 20).
3. The plates were blocked with blocking buffer (PBS containing 1% BSA), 200 l/well, for 1 hour at 37° C. with shaking.
4. After blocking, the plates were washed three times with washing buffer and 100 ml aliquots of tested samples, standard curve samples and check samples were added to the plates and incubated for 60 min at 37° C. with shaking.
5. Plates were washed again three times with washing buffer, and 100 ml of the detection antibody: biotinylated anti-IL6, were added to each well.
6. The plates were incubated for 60 min at 37° C. with shaking.
7. The plates were incubated with a second antibody, Avidin-HRP, following the same procedure described in steps 5-6 above.
8. Plates were washed three times with washing buffer.
9. 100 ml of substrate solution (TMB) was added to each well and the plates were incubating 20 min at room temperature (without shaking).
10. The reaction was stopped by adding 50 µl/well of stop solution (3N HCl).
11. The absorbance was measured at 450 nm in an ELISA reader.
12. Standard solutions were prepared by serial dilutions of the IL6 reference standard give a standard curve of 31.75-2000 µg/ml (linear range was between 31.75-500 µg/ml).
13. The optical density data results were processed and results calculated by the Magelan software. A robotic sample processor performed the dilution of samples, preparation of standard curve dilution series, and distribution of samples on the plate.

Collecting Anti-IL22RA Cell Culture Harvest for Analysis.

Producer Cells ($0.5 \times 10^6$) were seeded in 20 ml ProCHO5 medium in filter tube 50 and cultured for 24 hours at 37° C. on a shaker at 320 rpm. The harvest was centrifuged and filtrated throughout 0.22 µm filter. The clarified supernatant was analyzed by ELISA assay followed by Western blot assay.

ELISA for Anti-IL22.

The following procedure was employed:

1. Microtiter plates were coated with 100 µl per well of 2.0 µg/ml Goat anti-human IgG (H+L) in coating buffer and incubated overnight at ~4° C. in humid box. The plates can be stored in −20° C. for 3 months after O/N incubation.
2. The plates were washed four times with washing buffer (PBS containing 0.05% of Tween 20).
3. The plates were blocked with blocking buffer (BSA 1% in PBS-T 0.05%), 200 µl/well, for 1 hour at RT.
4. After blocking, the plates were washed four times with washing buffer and 100 µl aliquots of tested samples, standard curve (1.56-100 ng/ml) and check samples in assay buffer (Milk 1% in PBS×1). The plates were covered with a plate sealer and incubated for 60 min at 37° C. no shaking.
5. Plates were washed again four times with washing buffer, and 100 µl of the second antibody goat anti human IgG Fab HRP diluted 1:100,000 in assay buffer) were added to each well.
6. The plates were incubated for 60 min at 37° C.
7. Plates were washed four times with washing buffer and 100 µl of substrate solution (TMB) were added to each well and the plates were incubated 15-20 min at room temperature (without shaking).
8. The reaction was stopped by adding 100 µl/well of stop solution (1N HCl).
9. The absorbance was measured at A450 nm in an ELISA reader.
10. Standard solutions were prepared by serial dilutions of the Std. Anti-IL22RA MSB0010074/C12 in PBS, pH 6.0 to give a standard curve range from 1.56 to 100 ng/ml (linear range was between 1.56 to 50 ng/ml) in assay buffer. A sample of crude harvest from the relevant pool was diluted with assay buffer to obtain ~25 ng/ml and used as a check sample.

11. The optical density data results were processed and results calculated by the Magelan software.
12. The dilution of samples, preparation of standard curve dilution series, and distribution of samples on the plate was performed by a robotic sample processor.

SDS-PAGE/Western Blot Analysis.

Clarified supernatant samples of anti-IL22RA clones in ProCHO5 medium was diluted in SDS PAGE sample buffer. Samples of anti-Il22RA clones (0.1 gig per lane by ELISA) were separated on SDS-PAGE 10% Bis Tris gels under non-reducing conditions. The pre-stained MW protein standard (15 mel) was loaded on the gel as well. Electrophoresis was performed at constant voltage (100 V) for ~2 hr with a Novex Xcell SureLock Mini-Cell electrophoresis system. At the end of the SDS PAGE run the proteins were transferred from the gel to a nitrocellulose membrane in a blotting module with transfer buffer using power supply adjusted to 35 volt for 1 hour. The membrane was washed with PBS- 0.05% Tween 20 for 5 min, followed by incubation blocking buffer over night at 4° C. The membrane was incubated with the following antibodies diluted in working buffer, for 2 hours at room temperature with shaking: a) Goat anti-Human IgG Fc HRP b) Goat anti-Human kappa light chain followed by Donkey anti-goat HRP. The membrane was then washed in PBS-0.05% Tween 20 three times for 5 min each time. The bands were visualized by incubation in ECL reagent for 1 min following by exposure of a film in an AFP X-Ray Film Processor "Mini-Medical" developer. After developing the film was scanned.

Example 1. Platform Design

The platform design for evaluation of BMP and BAP expression levels on cell surface was created first with the reporter protein located on an individual expression cassette to insure sufficient expression and permit expression evaluation (FIG. 1; vectors MB-065, MB-066 & MB-067). After verification of reporter protein expression and detection on cell surface by FACS, new BMP containing vectors were constructed with a tight linkage between the BMP based reporter genes and the GOIs in a bicistronic mRNA. The plasmids were composed of the GOIs driven by the powerful human CMV (hCMV) promoter and the reporter gene was located downstream to the EMCV IRES. This architecture dictates transcription of both genes on the same mRNA [47] (FIG. 1; vectors MB-070-MB-076).

The reporter molecule contained a membrane bound protein or peptide and a reporter moiety (BMP or BAP). The first membrane bound protein was composed of the CD59a from mouse, which is a small protein of 101 amino acids [37] anchored via its C terminal end to the external side of the cell membrane by glycosyl phosphatidylinositol (GPI) [40] (vectors MB065, MB066, MB-070-MB-072 in FIG. 1). The nucleic acid sequence of the BMP-CD59a construct is as set forth in SEQ ID NO: 10). Alternatively, a synthetic peptide of 60 amino acids was created (SEQ ID NO: 1), with two potential N-glycosylation sites, that was anchored to the cell membrane via either a TM domain from mouse IGF-1 receptor (SEQ ID NO: 2; vector MB-073 & MB-075; FIG. 1) or a GPI anchorage domain from CD48 (Cys residues were replaced by Ser; SEQ ID NO: 3; vectors MB-074 & MB-076; FIG. 1). Prediction of TM domain sequence was done by TMHMM server v.2.0, [32] and GPI anchored sequence was done by GPI modification site prediction. [33-36] The N terminal end of the membrane protein or peptide or the GPI anchored signal are bound via a linker to either the BMP coding for amino acid sequence of CHPQGPPC [22, 23] (SEQ ID NO: 5) or the BAP coding for amino acid sequence of GLNDIFEAQKIEWHE [24] (SEQ ID NO: 13).

Cells transfected with BMP containing vectors were directly stained with fluorescently labeled streptavidin (F-SA, FIG. 2A). Staining of the BAP expressing cells was required prior to biotinylation of this reporter peptide. This was achieved by either co-transfection of the cells with CHO optimized BirA sequence [27] to obtain in-vivo biotinylation by the cell itself (data not shown) [27-29, 31, 48] or by in-vitro biotinylation of BAP on the cell surface by adding the bacterial enzyme BirA exogenously [30, 49] (FIG. 2B).

The platform was expanded in order to stringently select for cells producing high levels of the gene of interest by fusing BMP with the PAC resistance gene. The BMP-PAC permits puromycin selection after transfection followed by FACS selection according to the BMP levels. A plasmid was constructed for the expression of a model antibody, composed of two expression cassettes one for the heavy chain and one for the light chain. The heavy chain expression is driven by the powerful murine CMV IE2 (mCMV IE2) promoter and the reporter gene is located downstream to an EMCV IRES. The light chain expression is driven by the murine CMV IE1 (mCMV IE1) promoter and a QSy (glutamine synthetase) selection marker is located downstream to another EMCV IRES. This architecture dictates transcription of the heavy chain and BMP-PAC genes on a single mRNA and the transcription of the light chain and the QSy on another mRNA[47] (FIG. 3; vector MB98).

The reporter-selection molecule contains: the BMP preceeded by a signal peptide derived from murine CD59a molecule. The BMP is fused on its C terminus to a synthetic peptide of 60 amino acids, with two potential N-glycosylation sites. This synthetic carrier is linked to a TM domain from mouse IGF-I receptor. The TM domain is linked to the PAC selection resistance gene via a short linker (FIG. 2C, FIG. 3; vector MB-098). Prediction of TM domain sequence was done by TMHMM server v.2.0. The BMP is encoded by the amino acid sequence of SEQ ID NO: 5).

PAC in this specific construct is attached to the cell membrane. Therefore PAC has to contain efficient N acetylation activity as a membrane bound protein, which is different from its natural cytoplasmic state.

Example 2. Construction of Expression Vectors

For this project three sets of vectors were constructed at different stages of the project:

In the first set the biotin mimetic peptide (BMP), Biotin acceptor peptide (BAP) and BirA genes were cloned into vectors directly downstream to the hCMV promoter. These vectors were initially used to test the BMP and BAP expression level on cell surface and the ability to detect these markers with fluorescent streptavidin (F-SA) by FACS, and in later experiments as control vectors. The second set of vectors contained the BMP-CD59-GPI cassette downstream of an EMCV IRES thus linking the FACS selection marker to the GOI in a tighter and direct manner than in the vectors used before. The third set contained a synthetic peptide carrier instead of the mouse CD59a (which includes GPI), anchored to the cell membrane via GPI or TM domains (FIG. 1). As a selection marker the PAC gene was inserted in the vector downstream to the SV40 promoter, resulting in cytosolic PAC in the transfected cells.

All vectors were constructed according to known procedures as taught for example in F. M. Ausubel et al.[50].

Example 3. Evaluation of the Reporter Molecules for Sorting High POI Producer Cells 3.1 Expression and Detection of the Reporter Molecules on Cell Surface.

Generation of cells expressing GOI and BMP or GOI and BAP or GOI and BAP and BirA was done by LipofectAmine transfections of plasmids into CHO-S cells followed by selection with puromycin or puromycin and zeocin in cells co-transfected with BirA containing plasmid.

The stable pools were analyzed for expression levels of the reporter genes. BAP level was analyzed following biotinylation by BirA added exogenously and then labeled with F-SA (FIG. 4) or biotinylation intracellularly in those cells co-transfected with BirA, followed by labeling with F-SA (data not shown).

BMP level was analyzed directly by binding of F-SA. The results show specific fluorescence signal of the reporter molecules on the transfected cells with no significant background on non-transfected and non-labeled cells (FIG. 5A).

In FIG. 5, CHO-S cells, non-transfected and transfected with plasmids containing BMP-CD59a directly downstream to hCMV promoter (A) or downstream to EMCV IRES (B) were either stained, or not stained with F-SA and analyzed for their fluorescent labeling levels by FACS. The fluorescence level of the streptavidin-stained BMP (FIG. 5) is lower than that of the streptavidin-stained BAP (FIG. 4).

Possible reason for the difference in the fluorescent labeling intensity of cells stained with BMP and BAP could reside in the significantly lower affinity of the biotin mimetic peptide to streptavidin vs. natural biotin in the case of BAP (several order of magnitudes). In spite of this difference, high staining intensity of BMP expressing cells was obtained, significantly above background to enable sorting of the labeled cells by FACS.

Figure 5A:
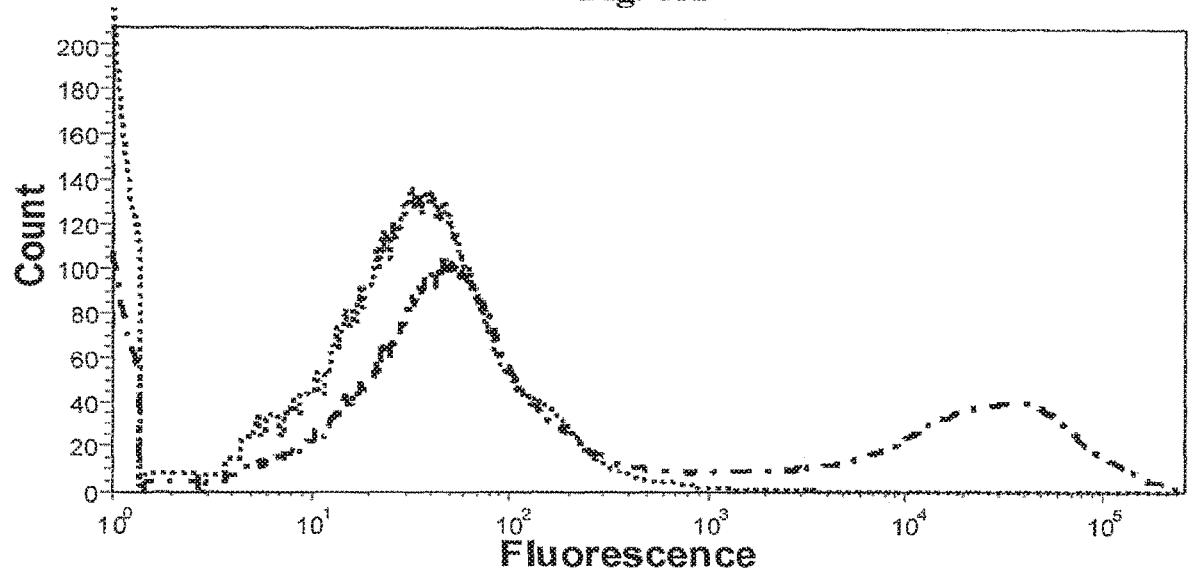
FIGS. 5A-B show detection of BMP on cell surface with F-SA by FACS. CHO-S cells, non-transfected ( . . . MFI—27) or transfected (- . -, MFI—10516) with plasmid containing BMP-CD59a directly downstream to hCMV promoter and stained with F-SA (A). CHO-S cells, non-transfected and not stained (—, MFI—66), non-transfected and stained with F-SA ( . . . , MFI—36), transfected with plasmid containing BMP-CD59a downstream to EMCV IRES and either not stained (- - -, MFI—63) or stained with F-SA (- . . -, MFI—1583) (B).
Figure 5B:
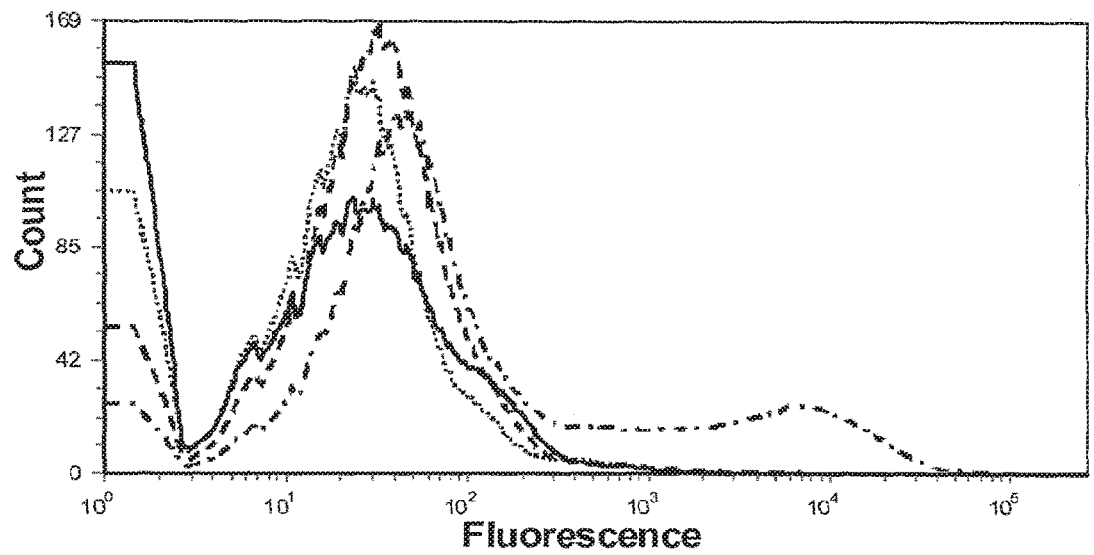
Figure 6A:
FIGS. 6A-C show CHO-S producer cells sorting with the BMP-CD59/F-SA system. Stable cells transfected with a vector containing sCD164-Fc (the POI) and BMP-CD59a (the reporter gene for FACS sorting) (A), were successively sorted three times according to their BMP levels indicated by the F-SA (B), not labeled and not sorted (—, MFI-102), labeled before sortings ( . . . , MFI—1734, PCD—1.59), after the first sort (- - -, MFI—8804, PCD—4.60) after the second sort (- . -, MFI—16691, PCD—5.79), and after the third sort (- . . - , MFI—18995, PCD—7.34). The correlation between fluorescence and productivity is shown (C). MFI, mean fluorescent intensity; PCD (specific productivity), Picogram per Cell per Day; EMCV, Encephalomyocarditis virus; IRES, Internal ribosome entry site; CD164-Fc, CD164 fused to Fcc region.
Figure 6B:
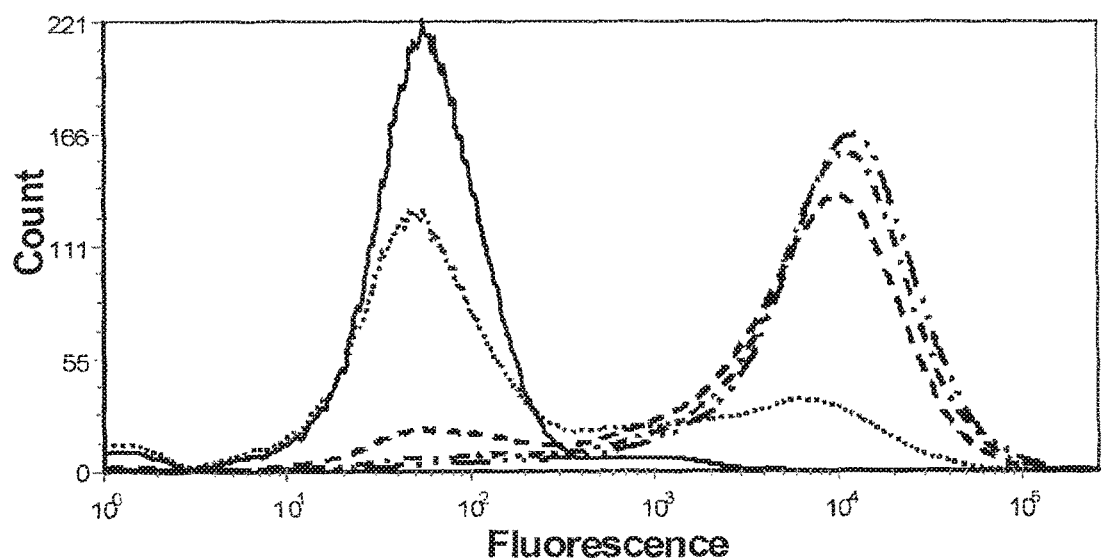
Figure 6C:
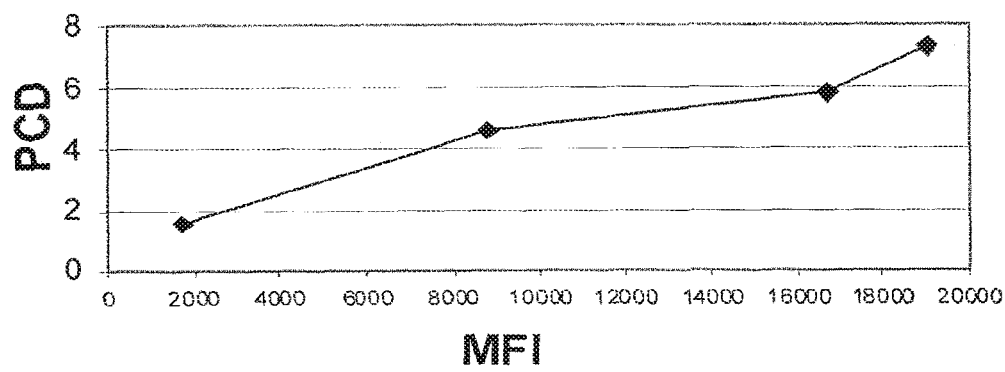
Figure 7A:
FIGS. 7A-C show CHO-S producer cells sorting with the BMP-CD59/F-SA system. Stable cells transfected with a vector containing GCSF (the POI) and BMP-CD59a (the reporter gene for FACS sorting) (A), were successively sorted three times according to their BMP levels indicated by the F-SA (B), not labeled and not sorted (—, MFI—104), labeled before sortings ( . . . , MFI—10406, PCD—3.83), after the first sort (- - -, MFI—16661, PCD—6.03) after the second sort (- . -, MFI—16983, PCD—6.67), and after the third sort (- . . - , MFI—17676, PCD—6.63). The correlation between fluorescence and productivity is shown (C). GCSF—Granulocyte colony-stimulating factor (Gene of interest).
Figure 7B:
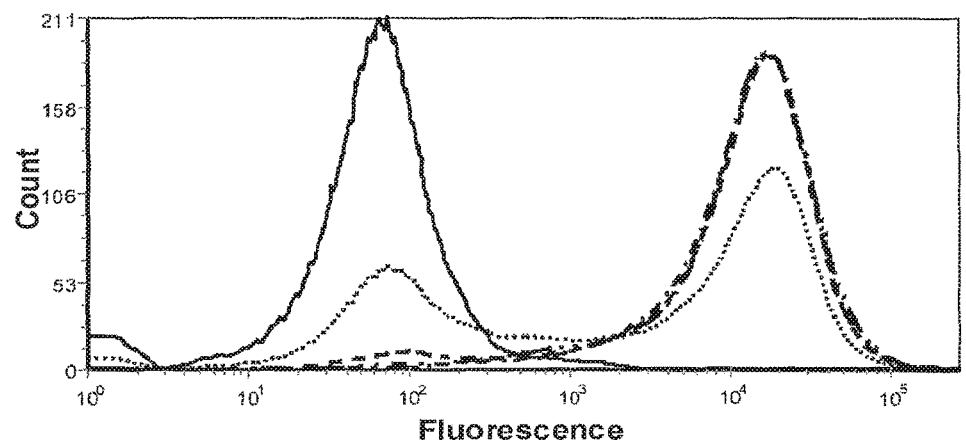
Figure 7C:
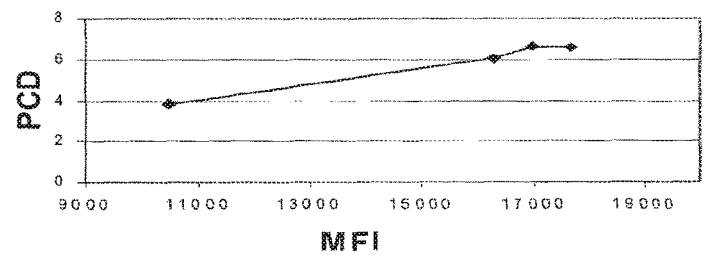
Figure 8A:
FIGS. 8A-C show CHO-S producer cells sorting with the BMP-CD59/F-SA system. Stable cells transfected with a vector containing the gene for IL-6 (the POI) and BMP-CD59a (the reporter gene for FACS sorting) (A), were successively sorted three times according to their BMP levels indicated by the F-SA (B), not labeled and not sorted (—, MFI—33), labeled before sortings ( . . . , MFI—246, PCD—0.4), after the first sort (- - -, MFI—1473, PCD—1.2) after the second sort (- . -, MFI—2812, PCD—1.7), and after the third sort (- . . . - , MFI—3642, PCD—1.8). The correlation between fluorescence and productivity is shown (C). IL-6-interleukin-6 (Gene of interest).
Figure 8B:
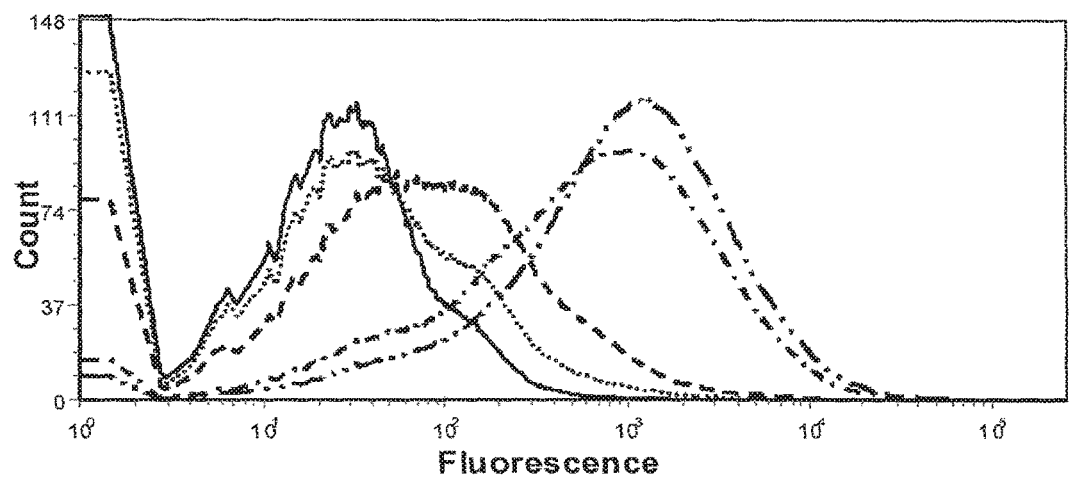
Figure 8C:
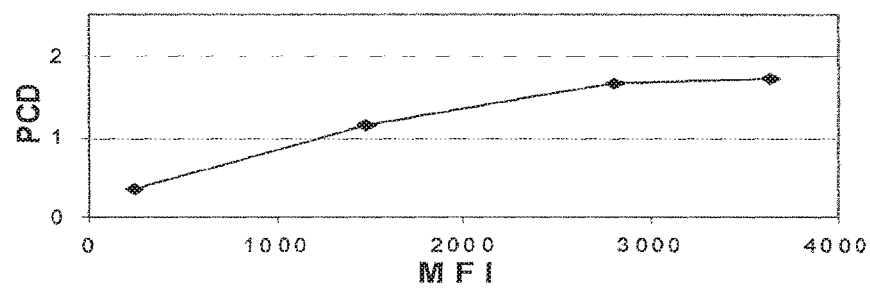
Figure 9A:
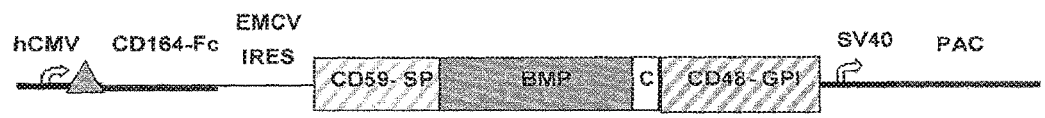
FIGS. 9A-C show CHO-S producer cells sorting with the BMP-P-GPI/F-SA System. Stable cells transfected with a vector containing CD164-Fc (the POI) and BMP-Peptide carrier (C)-GPI (the reporter gene for FACS sorting) (A), were successively sorted three times according to their BMP levels indicated by the F-SA (B), not labeled and not sorted (—, MFI—33), labeled before sortings ( . . . , MFI—773, PCD—0.8), after the first sort (- - -, MFI—9748, PCD—5.7) after the second sort (- . -, MFI—15492, PCD—9.5), and after the third sort (- . . . - , MFI—20908, PCD—10.8). The correlation between fluorescence and productivity is shown (C).
Figure 9B:
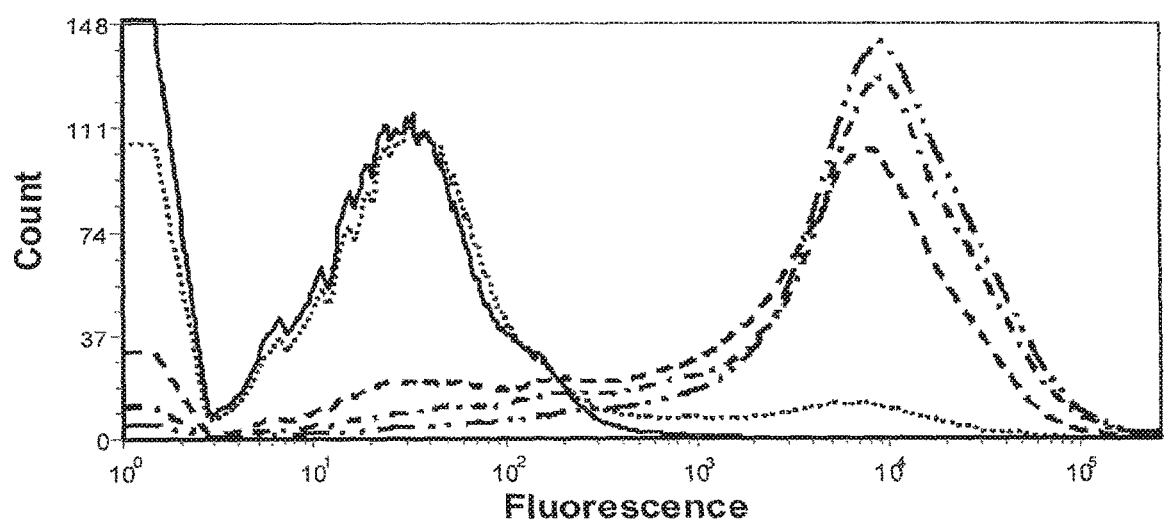
Figure 9C:
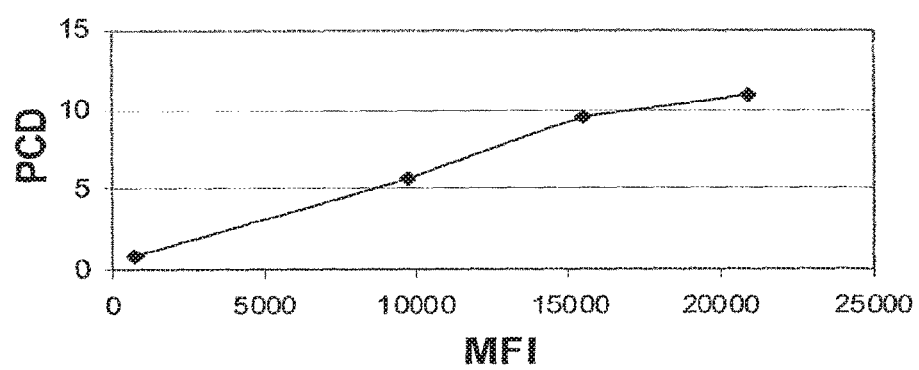
Figure 10A:
FIGS. 10A-C show CHO-S producer cells sorting with the BMP-P-GPI/F-SA System. Stable cells transfected with a vector containing GCSF (the POI) and BMP-Peptide carrier (C)-GPI (the reporter gene for FACS sorting) (A), were successively sorted three times according to their BMP levels indicated by the F-SA (B), not labeled and not sorted (—, MFI—113), labeled before sortings ( . . . , MFI—2326, PCD—3.0), after the first sort (- - -, MFI—7866, PCD—7.1) after the second sort (- . -, MFI—17497, PCD—9.2), and after the third sort (- . . . - , MFI—28679, PCD—13.0). The correlation between fluorescence and productivity is shown (C).
Figure 10B:
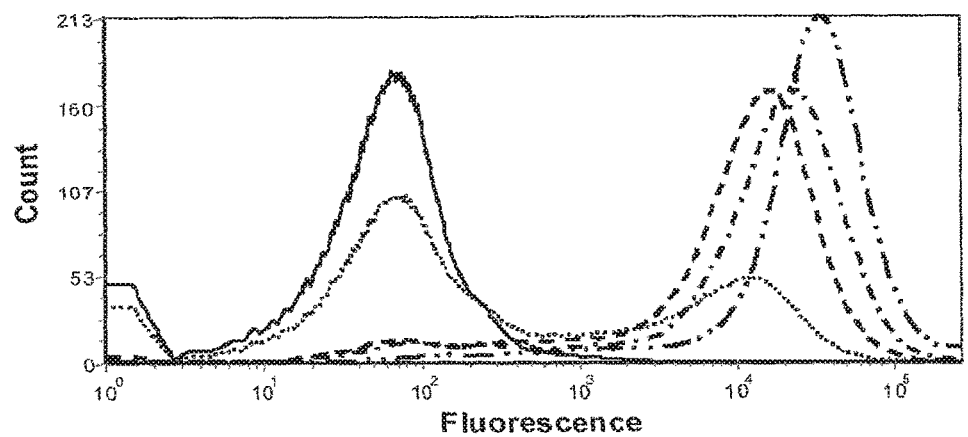
Figure 10C:
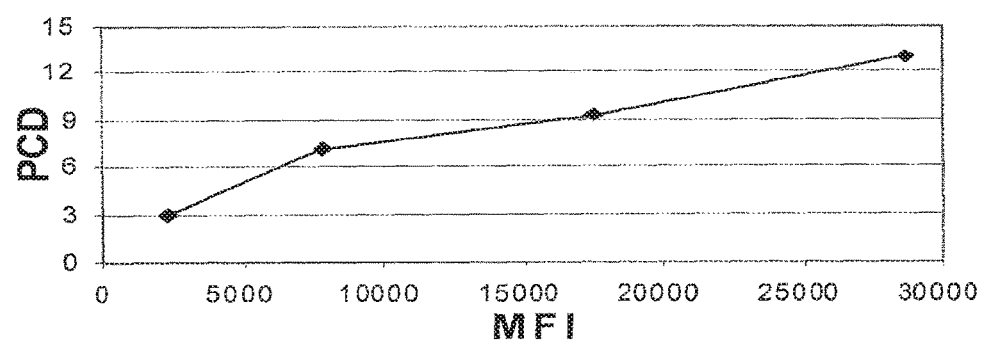
Figure 11A:
FIGS. 11A-C show CHO-S producer cells sorting with the BMP-P-IGF-IR-TM/F-SA System. Stable cells transfected with a vector containing CD164-Fc (the POI) and BMP-Peptide carrier (C)-TM (the reporter gene for FACS sorting) (A), were successively sorted three times according to their BMP levels indicated by the F-SA (B), not labeled and not sorted (—, MFI—33), labeled before sortings ( . . . , MFI—680, PCD—1.1), after the first sort (- - -, MFI—4719, PCD—7.0) after the second sort (- . -, MFI—7522, PCD—9.9), and after the third sort (- . . - , MFI—9113, PCD—12.0). The correlation between fluorescence and productivity is shown (C). TM—Trans-membrane peptide.
Figure 11B:
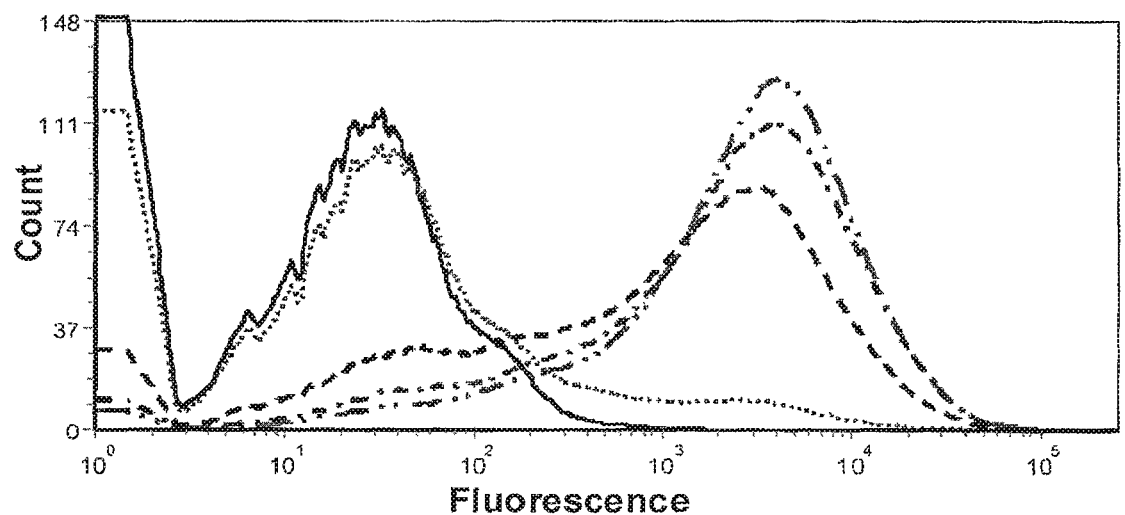
Figure 11C:
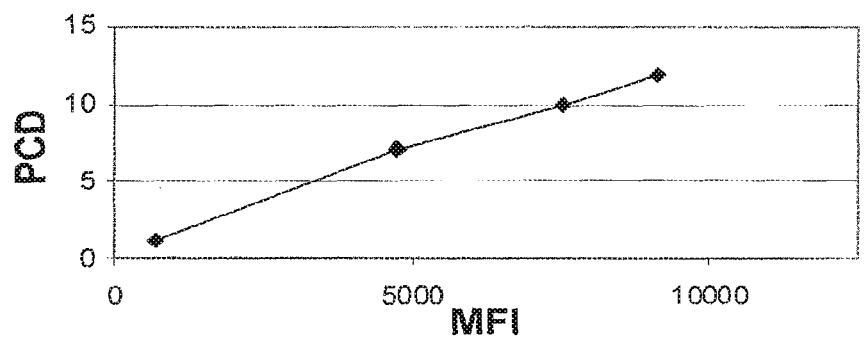
Figure 12A:
FIGS. 12A-C show CHO-S producer cells sorting with the BMP-P-IGF-IR-TM/F-SA System. Stable cells transfected with a vector containing GCSF (the POI) and BMP-Peptide carrier (C)-TM (the reporter gene for FACS sorting) (A), were successively sorted three times according to their BMP levels indicated by the F-SA (B), not labeled and not sorted (—, MFI—113), labeled before sortings ( . . . , MFI—4449, PCD—3.1), after the first sort (- - -, MFI—15764, PCD—7.1) after the second sort (- . -, MFI—26289, PCD—8.5), and after the third sort (- . . - , MFI—17367, PCD—12.0). The correlation between fluorescence and productivity is shown (C). TM—Trans-membrane peptide.
Figure 12B:
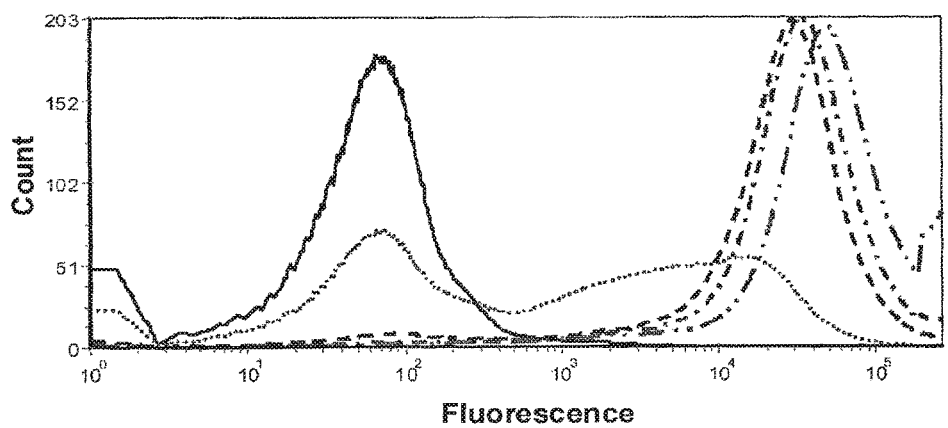
Figure 12C:
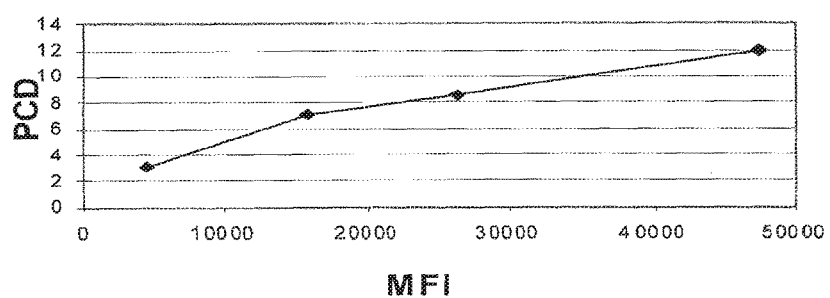

Two peaks with low and high fluorescence are seen in the transfected and labeled cells (FIGS. 5A-B; curves - . . - ). Those two peaks probably indicate low and high BMP expressers. It is speculated that the low expressers express also low levels of PAC even though the PAC is located on separated expression cassette. Nevertheless the PAC level is sufficient for the cells to survive under the puromycin selection pressure.

3.2 Sorting and Generation of High Producer Cells.

Cells were transfected with vector containing three different GOIs (sCD164-Fc, GCSF, IL-6) and the chimera of BMP-CD59a (vectors MB-070, MB-071, MB-072), BMP-Peptide carrier-GPI (vectors MB-074 & MB-076) or BMP-Peptide carrier-TM (vectors MB-073 & MB-075) (FIGS. 6-12) where the GOI and BMP are located on the same bicistronic expression cassette separated by an EMCV IRES. The stable pools generated by bio-selection with puromycin (expressed on a different cassette) were analyzed for the expression levels of the reporter molecules by FACS and the GOIs by specific ELISA.

Two peaks with low and high fluorescence are seen in the transfected and labeled cells (FIGS. 6-12; curves - . . - ). Those two peaks indicate low and high BMP expressers. It is speculated that the low expressers express also low levels of PAC. It is probable that the PAC level is sufficient for the cells to survive under the puromycin selection pressure but the BMP expression and possibly also the POI level of those cells is low.

In all cases (FIGS. 6-12) significant levels of BMP as well as the GOIs were detected. The cells were labeled with F-SA and the 4% highest fluorescent cells were sorted. The sorted cells were then propagated and analyzed for BMP and OOIs levels. The sorting procedure and analyses were successively repeated three times. In every sort the highest BMP expressed population was enriched, and as a consequence, the productivity level of the GOI was elevated (A positive correlation between the GOI and BMP expression levels was observed (FIG. 6 to FIG. 12).

Example 4. Construction of Expression Vectors Encoding for Reporter-PAC Fusion Product 4.1 Construction of Vector MB-098 (FIG. 3)—Vector MB-098 was Constructed According to Known Procedures as Taught for Example in F. M. Ausubel et al.[50].

4.2 Generation of Stable Pools Containing BMP-PAC Reporter, Evaluation of PAC Activity and Productivity Analysis.

Figure 13:
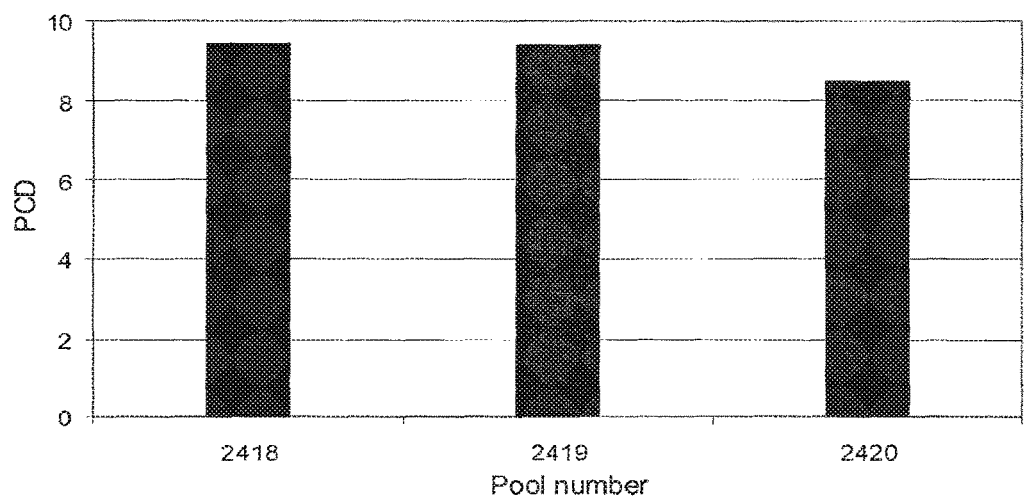
FIG. 13 shows productivity of pools transfected with a plasmid containing BMP-PAC (the reporter gene for FACS sorting); and anti-IL22RA mAb (the POI). CHO-S cells, transfected with a vector containing BMP-PAC and anti-IL22RA mAb in ProCHO5 were selected in 20 µg/ml puromycin and 25 µM MSX. Samples were taken for productivity determination.

CHO-S cells transfected in ProCHO5 with the BMP-PAC containing vector were subjected to selection with 20 µg/ml Puromycin (Invivogen, Cat. #ant-pr-1) and 25 µM MSX (Sigma Cat. #M5379). Under these conditions stable cells emerged which indicates that PAC is active in the membrane bound form. Stable pools express the anti-IL22RA mAb with specific productivity of 8.5-9.4 PCD (FIG. 13).

4.3 Sorting and Generation of High Producer Pools Containing BMP-PAC Reporter.

Figure 14:
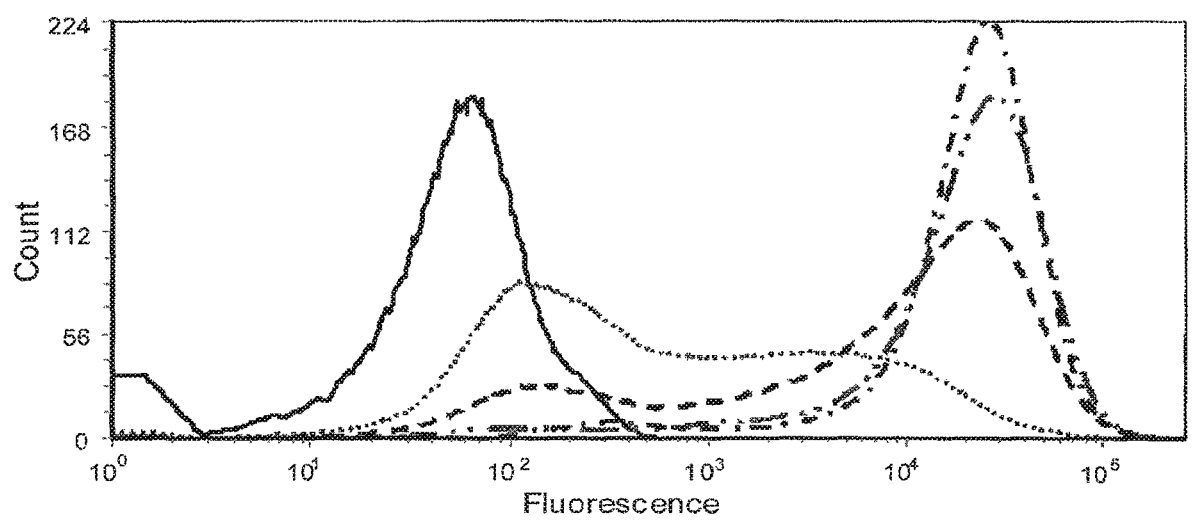
FIG. 14 shows CHO-S producer cells sorting with the BMP-PAC. Stable cells (3 replicates) transfected with a vector containing anti-IL22RA (the POI) mAb and BMP-PAC in ProCHO5 (the reporter gene for FACS sorting); were selected in 20 µg/ml Puromycin and 25 mM MSX and combined to united pools. United pools were successively sorted three times according to their BMP levels indicated by the F-SA. Pool not labeled and not sorted (—, MFI—67), labeled before sortings ( . . . , MFI—4449, PCD—3.1), after the first sort (- - -, MFI—15764, PCD—7.1) after the second sort (- . -, MFI—26289, PCD—8.5), and after the third sort (- . . - , MFI—17367, PCD—12.0).

The stable cells were analyzed and sorted by FACS in ProCHO5 medium (FIG. 14). Analyses show that BMP is detected in transfected pools. Two subpopulations are seen before sorts, which express high and low BMP levels. Consecutive sorts performed by selection of the 4% highest BMP expresser cells resulted in PCD elevation which was correlated with the BMP levels. Summary of results are seen in Table 1.

TABLE 1

Summary of sorting results using the BMP and BMP-PAC*.

| Reporter | GOI | MFI before sorts | MFI after sorts | PCD before sorts | PCD after sorts |
|---|---|---|---|---|---|
| BMP-CD59** | sCD164-Fc | 1734 | 18995 | 1.6 | 7.3 |
| BMP-CD59** | GCSF | 10406 | 17676 | 3.8 | 6.6 |
| BMP-CD59** | IL-6 | 246 | 3642 | 0.3 | 1.8 |
| BMP-IGF1-R-TM** | GCSF | 4449 | 47367 | 3.1 | 12.0 |
| BMP-CD48-GPI** | GCSF | 2326 | 28679 | 3.0 | 13.0 |
| BMP-IGF1-R-TM** | sCD164-Fc | 680 | 9113 | 1.1 | 12.0 |
| BMP-CD48-GPI** | sCD164-Fc | 773 | 20908 | 0.8 | 10.8 |
| BMP-IGF1-R-TM-PAC** | Anti-IL22RA mAb | 4449 | 17367 | 3.1 | 12.0 |

*Shown are the results of the mean fluorescence intensity (MFI) and POI levels before and after three sorts.
**Transfected cells were cultured in ProCHO5 medium Stable cells (3 replicates) transfected with a vector containing anti-IL22RA mAb and BMP-PAC in ProCHO5 (FIG. 14) were selected in 20 µg/ml Puromycin and 25 mM MSX and combined to united pools. The cells were analyzed for BMP level (red line). Pools were successively sorted three times according to their BMP levels labeled with F-SA. After each sorting cycle the cells were recovered and fluorescence as well as productivity were determined. The values of fluorescence level and productivity are shown in the brief description of FIG. 14.

3.5. Cloning of Sorted Pools by the FACS ACDU Device—Isolation of Clones.

Following three consecutive sorting cycles, The top ~4% fluorescent cells of anti-IL22RA mAb producing pools #2418UN-Hx3 in ProCHO5 were cloned by means of the Automated Cell Deposition Unit (ACDU) device of the FACSAria, which enables single cell cloning into 96 well plates. Cloning of cells grown in ProCHO5+20 mg/ml puromycin and 25 µM/ml MSX was done in 96 well plates containing 80% medium C6366 and 20% C6614. Colonies were detected by Cellavista at seeding day and then every 2-3 days. Wells with more than one colony were discarded. From cloning onward the culture media did not contain puromycin.

Figure 15:
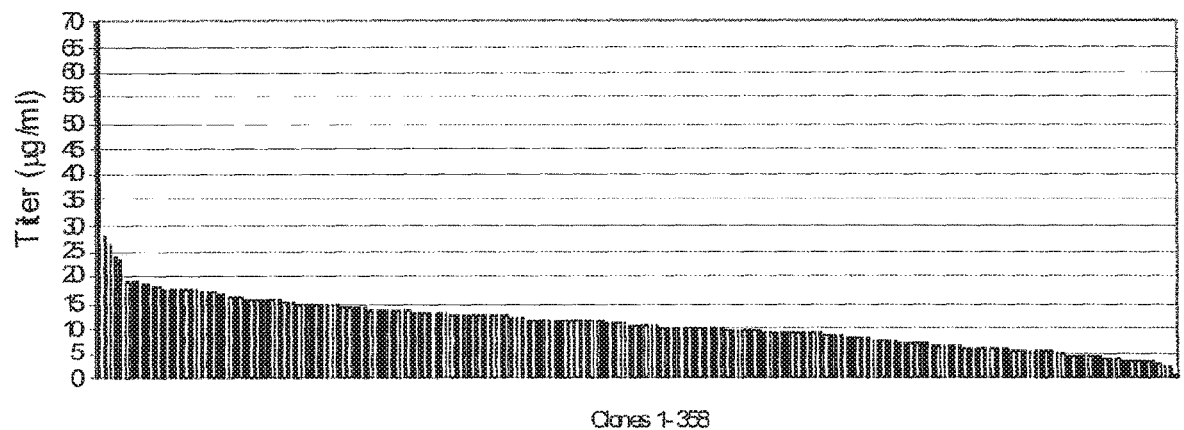
FIG. 15 shows titers obtained in clones transfected with BMP-PAC containing vector in medium containing ProCHO5. Accumulated titers of anti-IL22RA MAb (the POI) following cloning in 96 well plates. Cloning was done in 80% C6366+20% ProCHO5 and samples were taken for titer determination 13-15 days post cloning.
Figure 16:
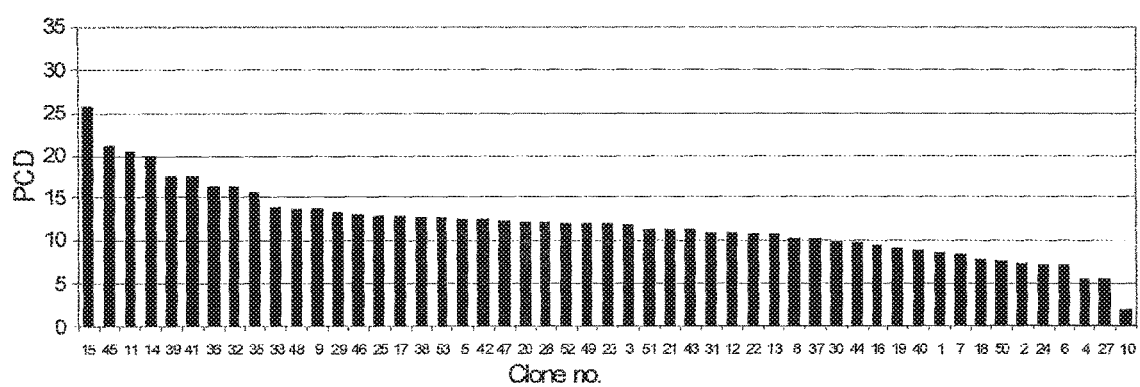
FIG. 16 shows specific productivity of clones transfected with BMP-PAC containing vector in ProCHO5 medium. Cells were seeded at $0.5 \times 10^6$ cells/ml ($10 \times 10^6$ cells) in ProCHO5 medium in 50 ml tubes for productivity measurements by ELISA. PCD—µg/cell/day.
Figure 17:
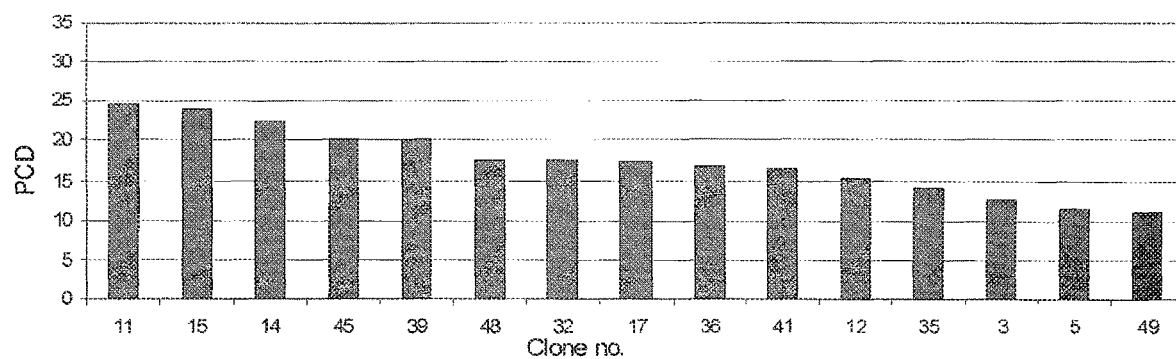
FIG. 17 shows specific productivity of clones transfected with BMP-PAC containing vector in ProCHO5 medium in the presence of 25 µM MSX. Cells were seeded at $0.5 \times 10^6$ cells/ml ($10 \times 10^6$ cells) in ProCHO5 medium containing 25 µM MSX in 50 ml tubes for productivity measurements by ELISA.

Supernatants from 358 wells were sampled and assayed for productivity (titer) by ELISA (FIG. 15). Forty clones derived from the pool with the highest titers were transferred first to T25 flasks and then to 50 ml tubes for evaluating specific productivity (FIG. 16). The best 15 clones derived from both pools were cultured with 25 µM MSX for evaluation of productivity in 50 ml tubes (FIG. 17).

3.6 Protein Product Identification in Crude Cell Culture Medium by SDS PAGE Western Blot.

Figure 18:
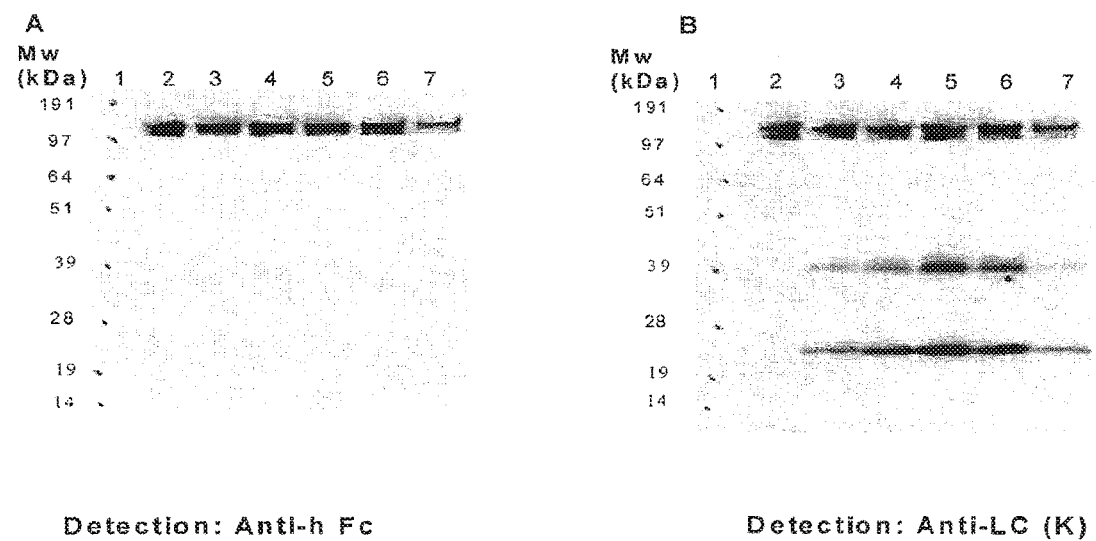
FIGS. 18A-B depict SDS PAGE/Western blot of mAb secreted by candidate clones in crude cell culture ProCHO-5 medium. Crude samples of candidate clones (100 ng of mAb per lane by ELISA) were separated by SDS-PAGE (10% BisTris) and transferred to nitrocellulose membrane. Detection was done with goat anti-human IgG Fc horse-radish-peroxidase (HRP) (A), and goat anti-human kappa light chain (B). ECL was the substrate for the HRP. The molecular weights of the markers (kDa) are shown to the left. The identification of the samples on the gels is as follows 1, MW marker; 2, Anti-IL22RA reference sample MSB0010074/C12; 3, Clone 2418-11; 4, Clone 2418-14; 5, Clone 2418-15; 6, Clone 2418-39; 7, Clone 2418-45.

The candidate clones were grown in ProCHO-5 medium. Product produced by those clones in the crude cell culture medium was analyzed (FIG. 18) by SDS-PAGE/Western blotting. Detection of the products was done with antibodies to human Fc and to the kappa light chain subunits of anti-IL22RA mAb (A and B respectively).

The results show that the intact product (heterodimer), with the apparent molecular weight of ~150 kDa was identified by both antibodies. In addition, free light chain secreted by all candidate clones (monomer and dimer according to apparent MW) was observed on the Western blots stained with the anti-LC (FIG. 18B).

Molecular weight of the heterodimer in the crude cell culture medium from all clones conforms to that of the purified product from the anti-IL22RA mAb reference sample. No significant difference in the apparent MW of the products of the different clones was found. Multiple bands may represent glycosylation micro-heterogeneity.

REFERENCES

1. Puck, T. T. and P. I. Marcus, *A Rapid Method for Viable Cell Titration and Clone Production with Hela Cells in Tissue Culture: The Use of X-Irradiated Cells to Supply Conditioning Factors*. Proc Natl Acad Sci USA, 1955. 41(7): p. 432-7.
2. Bohm, E., et al., *Screening for improved cell performance: selection of subclones with altered production kinetics or improved stability by cell sorting*. Biotechnol Bioeng, 2004. 88(6): p. 699-706.
3. Jun, S. C., et al., *Selection strategies for the establishment of recombinant Chinese hamster ovary cell line with dihydrofolate reductase-mediated gene amplification*. Appl Microbiol Biotechnol, 2005. 69(2): p. 162-9.
4. Coller, H. A. and B. S. Coller, *Poisson statistical analysis of repetitive subcloning by the limiting dilution technique as a way of assessing hybridoma monoclonality*. Methods Enzymol, 1986. 121: p. 412-7.
5. Underwood, P. A. and P. A. Bean, *Hazards of the limiting dilution methods of cloning hybridomas*. Journal of immunol. methods, 1987. 107: p. 119-128.
6. Herzenberg, L. A., et al., *The history and future of the fluorescence activated cell sorter and flow cytometry: a view from Stanford* Clin Chem, 2002. 48(10): p. 1819-27.
7. Browne, S. M. and M. Al-Rubeai, *Selection methods for high-producing mammalian cell lines*. Trends Biotechnol, 2007. 25(9): p. 425-32.
8. DeMaria, C. T., et al., *Accelerated clone selection for recombinant CHO CELLS using a FACS-based high-throughput screen*. Biotechnol Prog, 2007.23(2): p. 465-72.
9. Gaines, P. and D. M. Wojchowski, *pIRES-CD4t, a dicistronic expression vector for MACS-or FACS-based selection of transfected cells*. Biotechniques, 1999. 26(4): p. 683-8.
10. Meng, Y. G., et al., *Green fluorescent protein as a second selectable marker for selection of high producing clones from transfected CHO cells*. Gene, 2000. 242(1-2): p. 201-7.
11. Yoshikawa, T., et al., *Flow cytometry: an improved method for the selection of highly productive gene-amplified CHO cells using flow cytometry*. Biotechnol Bioeng, 2001. 74(5): p. 435-42.
12. Marder, P., et al., *Selective cloning of hybridoma cells for enhanced immunoglobulin production using flow cytometric cell sorting and automated laser nephelometry*. Cytometry, 1990. 11(4): p. 498-505.
13. Sen, S., W. S. Hu, and F. Srienc, *Flow cytometric study of hybridoma cell culture: correlation between cell surface fluorescence and IgG production rate*. Enzyme Microb Technol, 1990. 12(8): p. 571-6.
14. Brezinsky, S. C., et al., *A simple method for enriching populations of transfected CHO cells for cells of higher specific productivity*. J Immunol Methods, 2003. 277(1-2): p. 141-55.
15. Powell, K. T. and J. C. Weaver, *Gel microdroplets and flow cytometry: rapid determination of antibody secretion by individual cells within a cell population*. Biotechnology (N Y), 1990. 8(4): p. 333-7.
16. Weaver, J. C., P. McGrath, and S. Adams, *Gel microdrop technology for rapid isolation of rare and high producer cells*. Nat Med, 1997. 3(5): p. 583-5.
17. Frykman, S. and F. Srienc, *Quantitating secretion rates of individual cells: design of secretion assays*. Biotechnol Bioeng, 1998.59(2): p. 214-26.
18. Manz, R., et al., *Analysis and sorting of live cells according to secreted molecules, relocated to a cell-surface affinity matrix*. Proc Natl Acad Sci USA, 1995. 92(6): p. 1921-5.
19. Holmes, P. and M. Al-Rubeai, *Improved cell line development by a high throughput affinity capture surface display technique to select for high secretors*. J Immunol Methods, 1999. 230(1-2): p. 141-7.
20. Koller, M. R., et al., *High-throughput laser-mediated in situ cell purification with high purity and yield* Cytometry A, 2004. 61(2): p. 153-61.
21. Hanania, E. G., et al., *Automated in situ measurement of cell-specific antibody secretion and laser-mediated purification for rapid cloning of highly-secreting producers*. Biotechnol Bioeng, 2005. 91(7): p. 872-6.
22. Giebel, L. B., et al., *Screening of cyclic peptide phage libraries identifies ligands that bind streptavidin with high affinities*. Biochemistry, 1995. 34(47): p. 15430-5.
23. Katz, B. A., *Binding to protein targets of peptidic leads discovered by phage display: crystal structures of streptavidin-bound linear and cyclic peptide ligands containing the HPQ sequence*. Biochemistry, 1995. 34(47): p. 15421-9.

24. Beckett, D., E. Kovaleva, and P. J. Schatz, *A minimal peptide substrate in biotin holoenzyme synthetase-catalyzed biotinylation.* Protein Sci, 1999. 8(4): p. 921-9.
25. Barker, D. F. and A. M. Campbell, *The birA gene of Escherichia coli encodes a biotin holoenzyme synthetase.* J Mol Biol, 1981. 146(4): p. 451-67.
26. Chapman-Smith, A. and J. E. Cronan, Jr., *Molecular biology of biotin attachment to proteins.* J Nutr, 1999. 129(2S Suppl): p. 477S-484S.
27. Mechold, U., C. Gilbert, and V. Ogryzko, *Codon optimization of the BirA enzyme gene leads to higher expression and an improved efficiency of biotinylation of target proteins in mammalian cells.* J Biotechnol, 2005. 116(3): p. 245-9.
28. Parrott, M. B. and M. A. Barry, *Metabolic biotinylation of secreted and cell surface proteins from mammalian cells.* Biochem Biophys Res Commun, 2001. 281(4): p. 993-1000.
29. Yang, J., et al., *In vivo biotinylation of the major histocompatibility complex (MHC) class II/peptide complex by coexpression of BirA enzyme for the generation of MHC class II/tetramers.* Hum Immunol, 2004. 65(7): p. 692-9.
30. Chen, I., et al., *Site-specific labeling of cell surface proteins with biophysical probes using biotin ligase.* Nat Methods, 2005. 2(2): p. 99-104.
31. de Boer, E., et al., *Efficient biotinylation and single-step purification of tagged transcription factors in mammalian cells and transgenic mice.* Proc Natl Acad Sci USA, 2003. 100(13): p. 7480-5.
32. Krogh, A., et al., *Predicting transmembrane protein topology with a hidden Markov model: application to complete genomes.* J Mol Biol, 2001. 305(3): p. 567-80.
33. Eisenhaber, B., P. Bork, and F. Eisenhaber, *Sequence properties of GPI-anchored proteins near the omega-site: constraints for the polypeptide binding site of the putative transamidase.* Protein Eng, 1998. 11(12): p. 1155-61.
34. Sunyaev, S. R., et al., *PSIC: profile extraction from sequence alignments with position-specific counts of independent observations.* Protein Eng, 1999. 12(5): p. 387-94.
35. Eisenhaber, B., P. Bork, and F. Eisenhaber, *Prediction of potential GPI-modification sites inproprotein sequences.* J Mol Biol, 1999. 292(3): p. 741-58.
36. Eisenhaber, B., et al., *Automated annotation of GPI anchor sites: case study C. elegans.* Trends Biochem Sci, 2000. 25(7): p. 340-1.
37. Powell, M. B., et al., *Molecular cloning, chromosomal localization, expression, and functional characterization of the mouse analogue of human CD59.* J Immunol, 1997. 158(4): p. 1692-702.
38. Qian, Y. M., et al., *Identification and functional characterization of a new gene encoding the mouse terminal complement inhibitor CD59.* J Immunol, 2000. 165(5): p. 2528-34.
39. Sugita, Y. and Y. Masuho, *CD59: its role in complement regulation and potential for therapeutic use.* Immunotechnology, 1995. 1(3-4): p. 157-68.
40. Ikezawa, H., *Glycosylphosphatidylinositol (GPI)-anchored proteins.* Biol Pharm Bull, 2002. 25(4): p. 409-17.
41. Nielsen, H., et al., *Identification of prokaryotic and eukaryotic signal peptides and prediction of their cleavage sites.* Protein Eng, 1997. 10(1): p. 1-6.
42. Bendtsen, J. D., et al., *Improved prediction of signal peptides: Signal P 3.0.* J Mol Biol, 2004. 340(4): p. 783-95.
43. Urlaub, G. and L. A. Chasin, *Isolation of Chinese hamster cell mutants deficient in dihydrofolate reductase activity.* Proc Natl Acad Sci USA, 1980. 77(7): p. 4216-20.
44. Cockett, M. I., C. R. Bebbington, and G. T. Yarranton, *High level expression of tissue inhibitor of metalloproteinases in Chinese hamster ovary cells using glutamine synthetase gene amplification.* Biotechnology (N Y), 1990. 8(7): p. 662-7.
45. Page, M. J. and M. A. Sydenham, *High level expression of the humanized monoclonal antibody Campath-1H in Chinese hamster ovary cells.* Biotechnology (N Y), 1991. 9(1): p. 64-8.
46. Barnes, L. M., C. M. Bentley, and A. J. Dickson, *Advances in animal cell recombinant protein production: GS-NSO expression system.* Cytotechnology, 2000. 32(2): p. 109-23.
47. Gurtu, V., G. Yan, and G. Zhang, *IRES bicistronic expression vectors for efficient creation of stable mammalian cell lines.* Biochem Biophys Res Commun, 1996. 229(1): p. 295-8.
48. Viens, A., et al., *Use of protein biotinylation in vivo for chromatin immunoprecipitation.* Anal Biochem, 2004. 325(1): p. 68-76.
49. Cognet, I., et al., *Cardiotrophin-like cytokine labelling using Bir A biotin ligase: a sensitive tool to study receptor expression by immune and non-immune cells.* J Immunol Methods, 2005. 301(1-2): p. 53-65.
50. F. M. Ausbel, R. B., R. E. Kingston, D. D. Moore, J. G. Seidman, J. A. Smith, K. Struhl, ed. *Current protocols in molecular biology.* 2009, John Wiely & Sons, Inc.

The invention claimed is:

1. A method for the selection of eukaryotic cells secreting a protein of interest (POI), comprising identifying cells presenting Biotin Mimetic Peptide (BMP) comprising SEQ ID NO:5, on their cell surface, wherein the level of BMP presentation on the cell surface is correlated with the amount of POI secreted, the method comprising the steps of:
   (i) transfecting eukaryotic cells with a first eukaryotic vector comprising a nucleic acid molecule, said nucleic acid molecule comprising
      (I) a nucleic acid coding sequence comprising, (1) a first nucleic acid sequence encoding a signal peptide, (2) a second nucleic acid sequence encoding said BMP, (3) a third nucleic acid sequence encoding a polypeptide stretch that comprises a glycophosphatidylinositol (GPI) anchor attachment site that allows the anchorage of the BMP, by a GPI anchor attached to an amino acid of said attachment site, to a cell membrane, and (4) at least one expressible PO1-encoding nucleic acid sequence; and
      (II) a first promoter operably linked to said sequence (I) and capable of driving transcription of said sequence (I) in said eukaryotic cells;
   (ii) culturing said cells under conditions conducive to expression of said nucleic acid sequence (I) under the control of said promoter, and the expression product of said nucleic acid sequence (I) is processed by said cells to remove said signal peptide and to remove a portion of said GPI anchor attachment site and attach a GPI anchor to said amino acid of said attachment site which as a result of said removal is the C-terminal of the processed expression product, yielding a second post-translational product comprising said BMP that is anchored, by said GPI anchor attached to said amino acid of said GPI anchor attachment site, to the membranes of said cells, thereby establishing a stable pool of BMP-transfected cells;
   (iii) labeling the BMP-transfected cells with a detectable biotin-binding moiety; and
   (iv) identifying and isolating BMP-transfected cells labeled with the detectable biotin-binding moiety, thereby identifying cells expressing POL.

2. The method according to claim 1, further comprising propagating the isolated cells and repeating steps (i) to (iv).

3. The method according to claim 2, further comprising isolating a single cell labeled with the detectable biotin binding moiety and propagating the cell to form a clone.

4. The method according to claim 3, further comprising detecting and quantifying the secreted protein of interest, thereby selecting eukaryotic cells secreting a protein of interest.

5. The method according to claim 1, wherein said cells are mammalian cells.

6. The method according to claim 5, wherein the mammalian cells are selected from the group consisting of Chinese Hamster Ovary (CHO) cells, baby mouse myeloma NSO cells, hamster kidney (BHK) cells, human embryo kidney (HEK) cells, human retinal cells, COS cells, SP2/0 cells, WI38 cells, MRCS cells and Per.C6 cells.

7. The method according to claim 1, wherein the cells are labeled by contacting them with a detectable biotin-binding moiety selected from the group consisting of fluorescent avidin and fluorescent streptavidin.

8. The method according to claim 1, wherein the labeled cells are identified and isolated by the means of a FACS or magnet beads.

9. The method according to claim 7, wherein the selected eukaryotic cells present higher amounts of BMP on their surface and secrete larger amounts of protein of interest than the transfected cells of the stable pool.

10. The method according to claim 9, wherein the amount of BMP on the surface of the selected eukaryotic cells and the amount of protein of interest secreted by the selected eukaryotic cells are larger by at least a factor of two than the transfected cells of the stable pool.

11. The method of claim 1, wherein the GPI anchor attachment site is the mouse CD59a comprising SEQ ID NO:9, or a mutant CD48 comprising SEQ ID NO:3.

12. The method of claim 1, wherein the signal peptide is the mouse CD59a signal peptide comprising SEQ ID NO: 6.

13. The method of claim 1, wherein the first promoter is hCMV.

14. The method of claim 1, wherein the first vector further comprises a selectable marker.

15. The method of claim 14, wherein the selectable marker is puromycin N-acetyltransferase (PAC).

16. The method of claim 1, wherein said POI is a single polypeptide or a homopolymer of two or more identical polypeptides.

17. The method of claim 1, wherein said POI comprises two or more different polypeptide subunits, each encoded by a different POI-encoding nucleic acid sequence.

18. The method of claim 17, wherein the subunits are the light and heavy chains of an antibody.

19. The method of claim 1, wherein the POI is selected from the group consisting of IL-6, GCSF and CD164Fc.

20. The method of claim 11, wherein the signal peptide is the mouse CD59a signal peptide comprising SEQ ID NO: 6.

21. The method of claim 20, wherein the first vector further comprises a selectable marker.

22. The method of claim 21, wherein the selectable marker is puromycin N-acetyl transferase (PAC).

23. The method of claim 1, wherein said nucleic acid molecule further comprises an internal ribosome entry site (IRES).

24. The method of claim 23, wherein the IRES is the EMCV IRES.

25. A method for the selection of eukaryotic cells secreting a protein of interest (POI), comprising identifying cells presenting Biotin Mimetic Peptide (BMP) comprising SEQ ID NO:5, on their cell surface, wherein the level of BMP presentation on the cell surface is correlated with the amount of POI secreted, the method comprising the steps of:
   (i) transfecting eukaryotic cells with a first eukaryotic vector comprising a nucleic acid molecule, said nucleic acid molecule comprising
      (I) a nucleic acid coding sequence comprising, (1) a first nucleic acid sequence encoding a signal peptide, (2) a second nucleic acid sequence encoding said BMP, (3) a third nucleic acid sequence encoding a polypeptide stretch that comprises a transmembrane peptide that allows the anchorage of the BMP, by a GPI anchor attached to an amino acid of said attachment site, to a cell membrane, and (4) at least one expressible POI-encoding nucleic acid sequence; and
      (II) a first promoter operably linked to said sequence (I) and capable of driving transcription of said sequence (I) in said eukaryotic cells,
   (ii) culturing said cells under conditions conducive to expression of said nucleic acid sequence (I) under the control of said promoter, and the expression product of said nucleic acid sequence (I) is processed by said cells anchored, by said transmembrane peptide, to the membranes of said cells;

(iii) labeling the BMP-transfected cells with a detectable biotin-binding moiety; and (iv) identifying and isolating BMP-transfected cells labeled with the detectable biotin-binding moiety, thereby identifying cells expressing POL.

26. The method of claim 25, wherein the transmembrane peptide is the transmembrane peptide of mIGF-1 R comprising SEQ ID NO: 2.

* * * * *

SEQUENCE LISTING

```
<160> NUMBER OF SEQ ID NOS: 13

<210> SEQ ID NO 1
<211> LENGTH: 58
<212> TYPE: PRT
<213> ORGANISM: Artificial sequence
<220> FEATURE:
<223> OTHER INFORMATION: Synthetic

<400> SEQUENCE: 1

Gly Gly Gly Gly Ser Gly Gly Gly Ser Gly Ser Gly Ser Asn Ala
1               5                   10                  15

Thr Gly Thr Ser Gly Ser Gly Ser Gly Ser Gly Gly Thr Gly Ser
            20                  25                  30
```

Gly Gly Gly Gly Ser Gly Ser Gly Ser Asn Ala Thr Gly Gly Thr Thr
          35                  40                  45

Ser Gly Gly Gly Ser Gly Gly Thr Gly Ser
    50                  55

<210> SEQ ID NO 2
<211> LENGTH: 34
<212> TYPE: PRT
<213> ORGANISM: Artificial sequence
<220> FEATURE:
<223> OTHER INFORMATION: Synthetic

<400> SEQUENCE: 2

Glu Asn Phe Met His Leu Ile Ile Ala Leu Pro Val Ala Ile Leu Leu
1               5                   10                  15

Ile Val Gly Gly Leu Val Ile Met Leu Tyr Val Phe His Arg Lys Arg
            20                  25                  30

Asn Asn

<210> SEQ ID NO 3
<211> LENGTH: 38
<212> TYPE: PRT
<213> ORGANISM: Artificial sequence
<220> FEATURE:
<223> OTHER INFORMATION: Synthetic

<400> SEQUENCE: 3

Asn Asp Thr Val Tyr Phe Thr Leu Pro Cys Asp Leu Ala Arg Ser Ser
1               5                   10                  15

Gly Val Cys Trp Thr Ala Thr Trp Leu Val Val Thr Thr Leu Ile Ile
            20                  25                  30

His Arg Ile Leu Leu Thr
        35

<210> SEQ ID NO 4
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: REPEAT
<222> LOCATION: (1)..(5)
<223> OTHER INFORMATION: The sequence of residues 1-5 may be repeated 1
      to 5 times before the GGGG sequence
<220> FEATURE:
<221> NAME/KEY: VARIANT
<222> LOCATION: (6)..(9)
<223> OTHER INFORMATION: Residues 6 to 9 may be absent or present once.

<400> SEQUENCE: 4

Gly Gly Gly Gly Ser Gly Gly Gly Gly
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic

<400> SEQUENCE: 5

Cys His Pro Gln Gly Pro Pro Cys
1               5

<210> SEQ ID NO 6
<211> LENGTH: 23
<212> TYPE: PRT
<213> ORGANISM: Artificial sequence
<220> FEATURE:
<223> OTHER INFORMATION: Synthetic

<400> SEQUENCE: 6

Met Arg Ala Gln Arg Gly Leu Ile Leu Leu Leu Leu Leu Ala Val
1               5                   10                  15

Phe Cys Ser Thr Ala Val Ser
            20

<210> SEQ ID NO 7
<211> LENGTH: 198
<212> TYPE: PRT
<213> ORGANISM: Artificial sequence
<220> FEATURE:
<223> OTHER INFORMATION: Synthetic

<400> SEQUENCE: 7

Thr Glu Tyr Lys Pro Thr Val Arg Leu Ala Thr Arg Asp Asp Val Pro
1               5                   10                  15

Arg Ala Val Arg Thr Leu Ala Ala Ala Phe Ala Asp Tyr Pro Ala Thr
                20                  25                  30

Arg His Thr Val Asp Pro Asp Arg His Ile Glu Arg Val Thr Glu Leu
            35                  40                  45

Gln Glu Leu Phe Leu Thr Arg Val Gly Leu Asp Ile Gly Lys Val Trp
    50                  55                  60

Val Ala Asp Asp Gly Ala Ala Val Ala Val Trp Thr Thr Pro Glu Ser
65                  70                  75                  80

Val Glu Ala Gly Ala Val Phe Ala Glu Ile Gly Pro Arg Met Ala Glu
                85                  90                  95

Leu Ser Gly Ser Arg Leu Ala Ala Gln Gln Gln Met Glu Gly Leu Leu
            100                 105                 110

Ala Pro His Arg Pro Lys Glu Pro Ala Trp Phe Leu Ala Thr Val Gly
        115                 120                 125

Val Ser Pro Asp His Gln Gly Lys Gly Leu Gly Ser Ala Val Val Leu
    130                 135                 140

Pro Gly Val Glu Ala Ala Glu Arg Ala Gly Val Pro Ala Phe Leu Glu
145                 150                 155                 160

Thr Ser Ala Pro Arg Asn Leu Pro Phe Tyr Glu Arg Leu Gly Phe Thr
                165                 170                 175

Val Thr Ala Asp Val Glu Val Pro Glu Gly Pro Arg Thr Trp Cys Met
            180                 185                 190

Thr Arg Lys Pro Gly Ala
        195

<210> SEQ ID NO 8
<211> LENGTH: 1032
<212> TYPE: DNA
<213> ORGANISM: Artificial sequence
<220> FEATURE:
<223> OTHER INFORMATION: Synthetic

<400> SEQUENCE: 8
atgagagctc agagggact catcttactc ctgctgcttc tggctgtgtt ctgttccaca      60
gctgttagca tccctgtca cccacaggga cctccttgtg agggggcgg aagcggagga     120

| | |
|---|---|
| ggggggaagtg ggagtgggag taacgctacc gggacctccg ggtccggcgg cagtggaagc | 180 |
| ggaggaacag gaagtggagg aggggggaagt gggagtggaa gcaatgcaac cgggggaacc | 240 |
| acgtccgggg gcgggtccgg cggcacgggt agtgagaact tcatgcatct gatcattgct | 300 |
| ctgccggttg ccatcctgct gatcgttggg gggctggtta tcatgctgta tgtcttccat | 360 |
| agaaagagaa ataacggagg tggcgggagt ggtggtggcg gctctggcgg tggtgggtcc | 420 |
| ggtggaggtg gcagtaccga gtacaagccc acggtgcgcc tcgccacccg cgacgacgtc | 480 |
| ccccgggccg tacgcaccct cgccgccgcg ttcgccgact accccgccac gcgccacacc | 540 |
| gtcgacccgg accgccacat cgagcgggtc accgagctgc aagaactctt cctcacgcgc | 600 |
| gtcgggctcg acatcggcaa ggtgtgggtc gcggacgacg gcgccgcggt ggcggtctgg | 660 |
| accacgccgg agagcgtcga agcggggggcg gtgttcgccg agatcggccc gcgcatggcc | 720 |
| gagttgagcg gttcccggct ggccgcgcag caacagatgg aaggcctcct ggcgccgcac | 780 |
| cggcccaagg agcccgcgtg gttcctggcc accgtcggcg tctcgcccga ccaccagggc | 840 |
| aagggtctgg gcagcgccgt cgtgctcccc ggagtggagg cggccgagcg cgccggggtg | 900 |
| cccgccttcc tggagacctc cgcgccccgc aacctcccct tctacgagcg gctcggcttc | 960 |
| accgtcaccg ccgacgtcga ggtgcccgaa ggaccgcgca cctggtgcat gacccgcaag | 1020 |
| cccggtgcct ga | 1032 |

<210> SEQ ID NO 9
<211> LENGTH: 100
<212> TYPE: PRT
<213> ORGANISM: Artificial sequence
<220> FEATURE:
<223> OTHER INFORMATION: Synthetic

<400> SEQUENCE: 9

Leu Thr Cys Tyr His Cys Phe Gln Pro Val Val Ser Ser Cys Asn Met
1               5                   10                  15

Asn Ser Thr Cys Ser Pro Asp Gln Asp Ser Cys Leu Tyr Ala Val Ala
            20                  25                  30

Gly Met Gln Val Tyr Gln Arg Cys Trp Lys Gln Ser Asp Cys His Gly
        35                  40                  45

Glu Ile Ile Met Asp Gln Leu Glu Glu Thr Lys Leu Lys Phe Arg Cys
    50                  55                  60

Cys Gln Phe Asn Leu Cys Asn Lys Ser Asp Gly Ser Leu Gly Lys Thr
65                  70                  75                  80

Pro Leu Leu Gly Thr Ser Val Leu Val Ala Ile Leu Asn Leu Cys Phe
                85                  90                  95

Leu Ser His Leu
            100

<210> SEQ ID NO 10
<211> LENGTH: 485
<212> TYPE: DNA
<213> ORGANISM: Artificial sequence
<220> FEATURE:
<223> OTHER INFORMATION: Synthetic

<400> SEQUENCE: 10

| | |
|---|---|
| ggtaccgccc gacgcgtgcc accatgagag ctcagagggg actcatctta ctcctgctgc | 60 |
| ttctggctgt gttctgttcc acagctgtta gcatccctg tcaccacag ggacctcctt | 120 |
| gtggcggagg gggatccgga ggaggggggaa gtggggggcgg cggactcaca tgctatcact | 180 |

```
gtttccaacc ggtggtttct tcatgcaata tgaacagcac ttgctctcct gaccaggatt    240
cctgtctcta tgctgtagcc ggaatgcaag tgtatcaaag gtgttggaaa caatcagatt    300
gtcatggtga gatcattatg gaccaattag aagagacaaa attaaaattc agatgttgtc    360
agtttaactt gtgtaacaaa agtgacggat ccttggggaa gacaccattg ctggggacct    420
cggttctggt ggccattttg aatctttgtt tcttaagtca tctctaaaga tatcgcatca    480
agctt                                                                485

<210> SEQ ID NO 11
<211> LENGTH: 418
<212> TYPE: DNA
<213> ORGANISM: Artificial sequence
<220> FEATURE:
<223> OTHER INFORMATION: Synthetic

<400> SEQUENCE: 11
ggtaccccaa cgcgtgccac catgagagct cagaggggac tcatcttact cctgctgctt     60
ctggctgtgt tctgttccac agctgttagc atccctgtc acccacaggg acctccttgt    120 ggaggggggcg aagcggagg aggggggaagt gggagtggga gtaacgctac cgggacctcc    180
ggatccggcg gcagtggaag cggaggaaca ggaagtggag gaggggggaag tgggagtgga    240 agcaatgcaa ccgggggaac cacgtccggg ggcgggtccg gcggcacggg tagtgagaac    300
ttcatgcatc tgatcattgc tctgccggtt gccatcctgc tgatcgttgg ggggctggtt    360
atcatgctgt atgtcttcca tagaaagaga ataactaat gagatatcgg ataagctt      418

<210> SEQ ID NO 12
<211> LENGTH: 430
<212> TYPE: DNA
<213> ORGANISM: Artificial sequence
<220> FEATURE:
<223> OTHER INFORMATION: Synthetic

<400> SEQUENCE: 12
ggtaccccaa cgcgtgccac catgagagct cagaggggac tcatcttact cctgctgctt     60
ctggctgtgt tctgttccac agctgttagc atccctgtc acccacaggg acctccttgt    120 ggaggggggcg aagcggagg aggggggaagt gggagtggga gtaacgctac cgggacctcc    180
ggatccggcg gcagtggaag cggaggaaca ggaagtggag gaggggggaag tgggagtgga    240 agcaatgcaa ccgggggaac cacgtccggg ggcgggtccg gcggcacggg tagtaacgac    300
acagtgtact tcactctacc ttgtgatcta gccagatctt ctggagtatg ttggactgca    360
acttggctag tggtcacaac actcatcatt cacaggatcc tgttaaccta atgagatatc    420
ggataagctt                                                           430

<210> SEQ ID NO 13
<211> LENGTH: 15
<212> TYPE: PRT
<213> ORGANISM: Artificial sequence
<220> FEATURE:
<223> OTHER INFORMATION: Synthetic

<400> SEQUENCE: 13

Gly Leu Asn Asp Ile Phe Glu Ala Gln Lys Ile Glu Trp His Glu
1               5                   10                  15
```